(12) United States Patent
Ellsberry et al.

(10) Patent No.: US 6,544,261 B2
(45) Date of Patent: *Apr. 8, 2003

(54) SYSTEMS AND METHODS FOR ELECTROSURGICAL TREATMENT OF SUBMUCOSAL TISSUE

(75) Inventors: Maria B. Ellsberry, Fremont, CA (US); David C. Hovda, Mountain View, CA (US); Jean Woloszko, Mountain View, CA (US); Hira V. Thapliyal, Los Altos, CA (US); Philip E. Eggers, Dublin, OH (US)

(73) Assignee: ArthroCare Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/776,799

(22) Filed: Feb. 5, 2001

(65) Prior Publication Data

US 2001/0025176 A1 Sep. 27, 2001

Related U.S. Application Data

(60) Division of application No. 09/295,687, filed on Apr. 21, 1999, now Pat. No. 6,203,542, and a continuation-in-part of application No. 09/268,616, filed on Mar. 15, 1999, now Pat. No. 6,159,208, which is a continuation-in-part of application No. 09/054,323, filed on Apr. 2, 1998, now Pat. No. 6,063,079, and a continuation-in-part of application No. 09/083,526, filed on May 22, 1998, now Pat. No. 6,053,172, and a continuation-in-part of application No. 09/136,079, filed on Aug. 18, 1998, now Pat. No. 6,086,585, which is a continuation-in-part of application No. 08/990,374, filed on Dec. 15, 1997, now Pat. No. 6,109,268, which is a continuation-in-part of application No. 08/485,219, filed on Jun. 7, 1995, now Pat. No. 5,697,281.

(51) Int. Cl.[7] ............................................... A61B 18/14

(52) U.S. Cl. .............................. 606/41; 606/45; 606/46; 606/48; 606/50; 607/99; 607/105; 607/113; 604/114; 128/898

(58) Field of Search .............................. 606/41, 49, 50, 606/32, 45, 46, 48; 607/99, 105, 113, 122; 604/22, 114; 128/898

(56) References Cited

U.S. PATENT DOCUMENTS 2,050,904 A 8/1936 Trice .......................... 128/303

(List continued on next page.)

FOREIGN PATENT DOCUMENTS

| EP | 0703461 | 3/1996 | ........... G01R/27/02 |
| EP | 0740926 | 11/1996 | ........... A61B/17/39 |

(List continued on next page.)

OTHER PUBLICATIONS

C. Slager et al. (1987) *Z. Kardiologie* 76(6):67–71.
C. Slager et al. (1985) *JAAC* 5(6):1382–6.

(List continued on next page.)

*Primary Examiner*—Lee Cohen
(74) *Attorney, Agent, or Firm*—John T. Raffle; Sanjay S. Bagade

(57) ABSTRACT

The present invention provides systems and methods for selectively applying electrical energy to a target location within the head and neck of a patient's body, particularly including tissue in the ear, nose and throat. The present invention includes a channeling technique in which small holes or channels are formed within tissue structures in the mouth, such as the tonsils, tongue, palate and uvula, and thermal energy is applied to the tissue surface immediately surrounding these holes or channels to cause thermal damage to the tissue surface, thereby stiffening the surrounding tissue structure. Applicant has discovered that such stiffening of certain tissue structures in the mouth and throat helps to prevent the tissue structure from obstructing the patient's upper airway during sleep.

25 Claims, 30 Drawing Sheets

U.S. PATENT DOCUMENTS

| | | | |
|---|---|---|---|
| 4,033,351 A | 7/1977 | Hetzel | 128/303 |
| 4,040,426 A | 8/1977 | Morrison, Jr. | 128/303 |
| 4,043,342 A | 8/1977 | Morrison, Jr. | 128/303 |
| 4,116,198 A | 9/1978 | Roos | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,593,691 A | 6/1986 | Lindstrom et al. | 128/303.14 |
| 4,674,499 A | 6/1987 | Pao | 128/303 |
| 4,682,596 A | 7/1987 | Bales et al. | 604/22 |
| 4,706,667 A | 11/1987 | Roos | 128/303 |
| 4,765,331 A | 8/1988 | Petruzzi et al. | 128/303 |
| 4,823,791 A | 4/1989 | D'Amelio | 123/303 |
| 4,860,752 A | 8/1989 | Turner | 128/422 |
| 4,931,047 A | 6/1990 | Broadwin et al. | 604/22 |
| 4,936,301 A | 6/1990 | Rexroth et al. | 606/45 |
| 4,943,290 A | 7/1990 | Rexroth et al. | 606/45 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 128/303 |
| 5,035,696 A | 7/1991 | Rydell | 606/47 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/48 |
| 5,083,565 A | 1/1992 | Parins | 128/642 |
| 5,098,431 A | 3/1992 | Rydell | 606/48 |
| 5,108,391 A | 4/1992 | Flachenecker et al. | 606/38 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,196,007 A | 3/1993 | Ellman et al. | 606/32 |
| 5,197,963 A | 3/1993 | Parins | 606/46 |
| 5,217,457 A | 6/1993 | Delahuerga et al. | 606/42 |
| 5,249,585 A | 10/1993 | Turner | 607/99 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,290,282 A | 3/1994 | Casscells | 606/29 |
| 5,300,069 A | 4/1994 | Hunsberger et al. | 606/37 |
| 5,312,400 A | 5/1994 | Bales et al. | 606/41 |
| 5,314,406 A | 5/1994 | Arias et al. | 604/21 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,336,220 A | 8/1994 | Ryan et al. | 604/22 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,380,277 A | 1/1995 | Phillips | 604/33 |
| 5,383,876 A | 1/1995 | Nardella | 606/49 |
| 5,383,917 A | 1/1995 | Desai et al. | 607/702 |
| 5,395,312 A | 3/1995 | Desai | 604/22 |
| 5,395,368 A | 3/1995 | Ellman et al. | 606/45 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,812 A | 6/1995 | Ellman et al. | 606/45 |
| 5,441,499 A | 8/1995 | Fritzsch | 606/45 |
| 5,454,809 A | 10/1995 | Janssen | 606/41 |
| 5,456,662 A | 10/1995 | Edwards et al. | 604/22 |
| 5,458,596 A | 10/1995 | Lax et al. | 606/31 |
| 5,490,850 A | 2/1996 | Ellman et al. | |
| 5,505,728 A | 4/1996 | Ellman et al. | 606/39 |
| 5,505,730 A | 4/1996 | Edwards | 606/41 |
| 5,514,130 A | 5/1996 | Baker | 606/41 |
| 5,556,397 A | 9/1996 | Long et al. | 606/48 |
| 5,562,503 A | 10/1996 | Ellman et al. | 439/638 |
| 5,562,703 A | 10/1996 | Desai | 606/210 |
| 5,569,242 A | 10/1996 | Lax et al. | 606/42 |
| 5,571,101 A | 11/1996 | Ellman et al. | 606/45 |
| 5,584,872 A | 12/1996 | LaFontaine et al. | 607/116 |
| 5,609,151 A | 3/1997 | Mulier et al. | 128/642 |
| 5,624,439 A | 4/1997 | Edwards et al. | 606/45 |
| 5,630,812 A | 5/1997 | Ellman et al. | 606/41 |
| 5,647,869 A | 7/1997 | Goble | 606/37 |
| 5,658,278 A | 8/1997 | Imran et al. | 606/41 |
| 5,662,680 A | 9/1997 | Desai | 606/210 |
| 5,674,191 A | 10/1997 | Edwards et al. | 604/22 |
| 5,676,693 A | 10/1997 | LaFontaine | 607/116 |
| 5,681,282 A | 10/1997 | Eggers et al. | 604/114 |
| 5,683,366 A | 11/1997 | Eggers et al. | 604/114 |
| 5,683,386 A | 11/1997 | Ellman et al. | 606/41 |
| 5,683,387 A | 11/1997 | Garito | 606/45 |
| 5,695,495 A | 12/1997 | Ellman et al. | 606/41 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta | 606/48 |
| 5,707,349 A | 1/1998 | Edwards | 604/22 |
| 5,718,702 A | 2/1998 | Edwards | 606/41 |
| 5,725,524 A | 3/1998 | Mulier et al. | 606/41 |
| 5,728,094 A | 3/1998 | Edwards | 606/41 |
| 5,733,282 A | 3/1998 | Ellman et al. | 606/45 |
| 5,738,114 A | 4/1998 | Edwards | 128/889 |
| 5,746,224 A | 5/1998 | Edwards | 128/898 |
| 5,749,869 A | 5/1998 | Lindenmeier | 606/34 |
| 5,766,153 A | 6/1998 | Eggers et al. | 604/114 |
| 5,775,338 A | 7/1998 | Hastings | 128/898 |
| 5,800,379 A | 9/1998 | Edwards | 604/22 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,817,049 A | 10/1998 | Edwards | 604/22 |
| 5,820,580 A | 10/1998 | Edwards et al. | 604/22 |
| 5,823,197 A | 10/1998 | Edwards | 128/898 |
| 5,827,277 A | 10/1998 | Edwards | 606/41 |
| 5,843,021 A | 12/1998 | Edwards et al. | 604/22 |
| 5,843,077 A | 12/1998 | Edwards | 606/41 |
| 5,871,469 A | 2/1999 | Eggers et al. | 604/114 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,897,553 A | 4/1999 | Mulier et al. | 606/41 |
| 5,921,983 A | 7/1999 | Shannon, Jr. | 606/45 |
| 5,944,715 A | 8/1999 | Goble et al. | 606/41 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,027,501 A | 2/2000 | Goble et al. | 606/41 |
| 6,039,734 A | 3/2000 | Goble et al. | 606/41 |

| | | | |
|---|---|---|---|
| 6,056,746 A | 5/2000 | Goble et al. | 606/48 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,203,542 B1 * | 3/2001 | Ellsberry et al. | 128/898 |

FOREIGN PATENT DOCUMENTS

| | | | |
|---|---|---|---|
| EP | 0754437 | 1/1997 | A61B/17/39 |
| GB | 2308979 | 7/1997 | A61B/17/39 |
| GB | 2308980 | 7/1997 | A61B/17/36 |
| GB | 2308981 | 7/1997 | A61B/17/39 |
| GB | 2327350 | 1/1999 | A61B/17/39 |
| GB | 2327351 | 1/1999 | A61B/17/39 |
| GB | 2327352 | 1/1999 | A61B/17/39 |
| JP | 57-117843 | 7/1982 | A61B/17/39 |
| WO | WO 90/07303 | 7/1990 | A61B/17/39 |
| WO | WO 92/21278 | 12/1992 | A61B/5/04 |
| WO | 93/20747 | 10/1993 | A61B/5/00 |
| WO | 94/04220 | 3/1994 | A61N/1/06 |
| WO | 94/08654 | 4/1994 | A61M/37/00 |
| WO | 96/00042 | 1/1996 | A61B/17/39 |
| WO | 97/00646 | 1/1997 | A61B/17/39 |
| WO | 97/00647 | 1/1997 | A61B/17/39 |
| WO | 97/24073 | 7/1997 | A61B/17/39 |
| WO | 97/24993 | 7/1997 | A61B/17/39 |
| WO | 97/24994 | 7/1997 | A61B/17/39 |
| WO | 97/30644 | 8/1997 | A61B/17/39 |
| WO | 97/30645 | 8/1997 | A61B/17/39 |
| WO | 97/30646 | 8/1997 | A61B/17/39 |
| WO | 97/30647 | 8/1997 | A61B/17/39 |
| WO | 97/41785 | 11/1997 | A61B/17/39 |
| WO | 97/41786 | 11/1997 | A61B/17/39 |
| WO | 97/41787 | 11/1997 | A61B/17/39 |
| WO | 97/41788 | 11/1997 | A61B/17/39 |
| WO | 97/43969 | 11/1997 | A61B/17/39 |
| WO | 97/43970 | 11/1997 | A61B/17/39 |
| WO | 97/43972 | 11/1997 | A61B/17/39 |
| WO | 97/43973 | 11/1997 | A61B/17/39 |
| WO | 97/44092 | 11/1997 | A61N/1/40 |
| WO | 97/48346 | 12/1997 | A61B/17/39 |
| WO | WO 98/27879 | 7/1998 | A61B/17/36 |
| WO | 99/08613 | 2/1999 | A61B/17/36 |

OTHER PUBLICATIONS

P. Nardella (1989) *SPIE* 1068:42–49.

Elsasser et al. (1976) *Medizinal–Markt/Acta Medicotechna* 24(4):129–134.

E. Kramolowsky et al. (1991) *J. of Urology* 146:669–674.

R. Tucker et al. (1990) *Urol. Res.* 18:291–294.

R. Tucker et al. (1989) *J. of Urology* 141:662–665.

R. Tucker et al. (1989) Abstract P14–11, 7th World Congress on Endourology and ESWL, Nov. 27–30, 1989, Kyoto, Japan.

Rand et al. (1985) *J. Arthro. Surg.* 1:242–246.

J. Pearce *Electrosurgery*, John Wiley & Sons, New York, 1986.

* cited by examiner

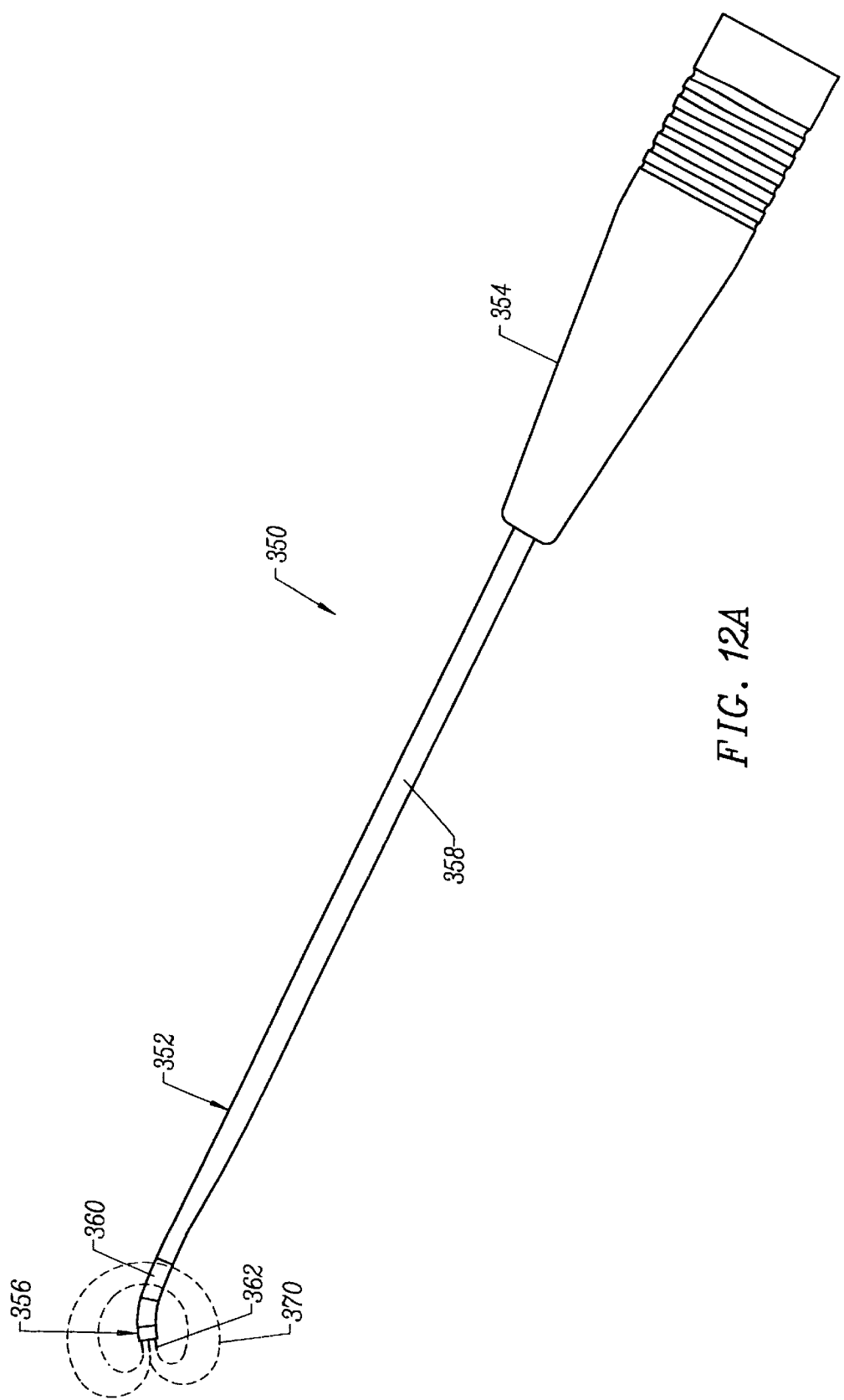

SYSTEMS AND METHODS FOR ELECTROSURGICAL TREATMENT OF SUBMUCOSAL TISSUE

RELATED APPLICATIONS

This application is a division of and claims the benefit of U.S. application Ser. No. 09/295,687, filed Apr. 21, 1999, now U.S. Pat. No. 6,203,542, and a continuation-in-part of U.S. patent application Ser. No. 09/268,616, filed Mar. 15, 1999, now U.S. Pat. No. 6,159,208 which is a continuation-in-part of U.S. patent application Ser. No. 09/054,323, filed Apr. 2, 1998, now U.S. Pat. No. 6,063,079 and Ser. No. 09/083,526 filed May 22, 1998, now U.S. Pat. No. 6,053,172 and Ser. No. 09/136,079 filed Aug. 18, 1998, now U.S. Pat. No. 6,086,585, each of which are continuation-in-parts of Ser. No. 08/990,374, filed Dec. 15, 1997, now U.S. Pat. No. 6,109,268, which is a continuation-in-part of U.S. patent application Ser. No. 08/485,219, filed on Jun. 7, 1995, now U.S. Pat. No. 5,697,281, the complete disclosures of which are incorporated herein by reference for all purposes.

The present invention is related to commonly assigned co-pending U.S. patent application Ser. No. 09/058,571, filed on Apr. 10, 1998, now U.S. Pat. No. 6,142,992 and U.S. patent application Ser. No. 09/074,020, filed on May 6, 1998, U.S. patent application Ser. No. 09/010,382, filed Jan. 21, 1998, now U.S. Pat. No. 6,190,381, and U.S. patent application Ser. No. 09/032,375, filed Feb. 27, 1998, U.S. patent application Ser. No. 08/977,845, filed on Nov. 25, 1997, now U.S. Pat. No. 6,210,402, Ser. No. 08/942,580, filed on Oct. 2, 1997, now U.S. Pat. No. 6,159,194, Ser. No. 09/026,851, filed Feb. 20, 1998, now U.S. Pat. No. 6,277,112, U.S. application Ser. No. 08/753,227, filed on Nov. 22, 1996, now U.S. Pat. No. 5,873,855 U.S. application Ser. No. 08/687792, filed on Jul. 18, 1996 and PCT International Application, U.S. National Phase Serial No. PCT/US94/05168, filed on May 10, 1994, now U.S. Pat. No. 5,697,909 which was a continuation-in-part of U.S. patent application No. 08/059,681, filed on May 10, 1993, now abandoned which was a continuation-in-part of U.S. patent application Ser. No. 07/958,977, filed on Oct. 9, 1992, now U.S. Pat. No. 5,366,443 which was a continuation-in-part of U.S. patent application Ser. No. 07/817,575, filed on Jan. 7, 1992, now abandoned, the complete disclosures of which are incorporated herein by reference for all purposes. The present invention is also related to commonly assigned U.S. Pat. No. 5,697,882, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat tissue in regions of the head and neck, such as the ear, nose and throat. The present invention is particularly suited for treating obstructive sleep disorders, such as sleep-apnea, snoring and the like.

Sleep-apnea syndrome is a medical condition characterized by daytime hypersomnolence, intellectual deterioration, cardiac arrhythmias, snoring and thrashing during sleep. This syndrome is typically divided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway.

Treatment for sleep apnea has included various medical, surgical and physical measures. Medical measures include the use of medications and the avoidance of central nervous system depressants, such as sedatives or alcohol. These measures are sometimes helpful, but rarely completely effective. Physical measures have included weight loss, opening nasopharygeal airways, nasal CPAP and various tongue retaining devices used nocturnally. These measures are cumbersome, uncomfortable and difficult to use for prolonged periods of time. In particular, CPAP devices, which act essentially as a pneumatic "splint" to the airway to alleviate the obstruction, must be used for the entire patient's lifetime, and typically requires close to 100% usage of the device while sleeping and napping. These factors result in limited patient compliance with CPAP devices, reducing the effectiveness of the therapy.

Surgical interventions have included uvulopalatopharyngoplasty (UPPP), laser-assisted uvuloplasty procedures (LAUP), tonsillectomy, surgery to correct severe retrognathia and tracheostomy. The LAUP procedures involve the use a $CO_2$ laser to excise and vaporize excess tissue in the region of the palate and uvula. In UPPP procedures, a scalpel or conventional electrocautery device is typically employed to remove portions of the uvula, palate, pharynx and/or tonsils. While these procedures are effective, the risk of surgery in some patients is often prohibitive. In addition, UPPP and LAUP procedures performed with conventional electrocautery or laser devices typically generate extreme post-operative pain which may be unacceptable to the patient.

Recently, RF energy has been used to selectively destroy portions of the tongue and soft palate to treat air passage disorders, such as sleep apnea. This procedure, which was developed by Somnus Medical Technologies of Sunnyvale, Calif., involves the use of a monopolar electrode that directs RF current into the target tissue to desiccate or destroy submucosal tissue in the patient's mouth. Of course, such monopolar devices suffer from the disadvantage that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue or neighboring peripheral nerves.

Another disadvantage of conventional RF devices, such as the Somnus monopolar electrode, is that these devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Yet another disadvantage with the Somnus technology is that the procedure typically takes a long time, often requiring the electrical energy to be applied to the submucosal tissue for a period of longer than a minute. This can be quite uncomfortable to the patient, who is typically awake during the procedure.

SUMMARY OF THE INVENTION

The present invention provides systems, apparatus and methods for selectively applying electrical energy to structures in the head and neck of a patient's body, such as tissue within the ear, nose and throat. The systems and methods of the present invention are particularly useful for treating obstructive sleep disorders, such as snoring or sleep apnea. The present invention includes a channeling technique in which small holes or channels are formed within tissue structures in the mouth, such as the tonsils, tongue, palate and uvula, and thermal energy is applied to the tissue surface immediately surrounding these holes or channels to cause thermal damage to the tissue surface, thereby stiffening the surrounding tissue structure. Applicant has discovered that such stiffening of certain tissue structures in the mouth and throat helps to prevent the tissue structure from obstructing the patient's upper airway during sleep.

Methods of the present invention include introducing one or more active electrode(s) into the patient's mouth, and positioning the active electrode(s) adjacent the target tissue, e.g., selected portions of the tongue, tonsils, soft palate tissues (e.g., the uvula and pharynx), hard tissue or other mucosal tissue. High frequency voltage is applied between the active electrode(s) and one or more return electrode(s) to volumetrically remove or ablate at least a portion of the target tissue, and the active electrode(s) are advanced through the space left by the ablated tissue to form a channel, hole, divot or other space in the target tissue. The active electrode(s) are then removed from the channel, and other channels or holes may be formed at suitable locations in the patient's mouth or throat. In preferred embodiments, high frequency voltage is applied to the active electrode(s) as they are removed from the hole or channel. The high frequency voltage is below the threshold for ablation of tissue to effect hemostasis of severed blood vessels within the tissue surface surrounding the hole. In addition, the high frequency voltage effects a controlled depth of thermal heating of the tissue surrounding the hole to thermally damage at least the surface of this tissue without destroying or otherwise debulking the underlying tissue. This thermal damage stiffens the tissue structure, thereby reducing obstructions to the patient's air passages.

In a specific configuration, electrically conductive media, such as isotonic saline or an electrically conductive gel, is delivered to the target site within the mouth to substantially surround the active electrode(s) with the media. The media may be delivered through an instrument to the specific target site, or the entire target region may be filled with conductive media such that the electrode terminal(s) are submerged during the procedure. Alternatively, the distal end of the instrument may be dipped or otherwise applied to the conductive media prior to introduction into the patient's mouth. In all of these embodiments, the electrically conductive media is applied or delivered such that it provides a current flow path between the active and return electrode(s). In other embodiments, the intracellular conductive fluid in the patient's tissue may be used as a substitute for, or as a supplement to, the electrically conductive media that is applied or delivered to the target site. For example, in some embodiments, the instrument is dipped into conductive media to provide a sufficient amount of fluid to initiate the requisite conditions for ablation. After initiation, the conductive fluid already present in the patient's tissue is used to sustain these conditions.

In the representative embodiments, the active electrode(s) are advanced into the target tissue in the ablation mode, where the high frequency voltage is sufficient to ablate or remove the target tissue through molecular dissociation or disintegration processes. In these embodiments, the high frequency voltage applied to the electrode terminal(s) is sufficient to vaporize an electrically conductive fluid (e.g., gel, saline and/or intracellular fluid) between the electrode terminal(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,697,882 the complete disclosure of which is incorporated herein by reference.

The active electrode(s) are usually removed from the holes or channels in the subablation or thermal heating mode, where the high frequency voltage is below the threshold for ablation as described above, but sufficient to coagulate severed blood vessels and to effect thermal damage to at least the surface tissue surrounding the holes. In some embodiments, the active electrode(s) are immediately removed from the holes after being placed into the subablation mode. In other embodiments, the physician may desire to control the rate of removal of the active electrode(s) and/or leave the active electrode(s) in the hole for a period of time, e.g., on the order of about 1 to 10 seconds, in the subablation mode to increase the depth of thermal damage to the tissue.

In one method, high frequency voltage is applied, in the ablation mode, between one or more active electrode(s) and a return electrode spaced axially from the active electrode (s), and the active electrode(s) are advanced into the tissue to form a hole or channel as described above. High frequency voltage is then applied between the return electrode and one or more third electrode(s), in the thermal heating mode, as the electrosurgical instrument is removed from the hole. In one embodiment, the third electrode is a dispersive return pad on the external surface of the skin. In this embodiment, the thermal heating mode is a monopolar mode, in which current flows from the return electrode, through the patient's body, to the return pad. In other embodiments, the third electrode(s) are located on the electrosurgical instrument and the thermal heating mode is bipolar. In all of the embodiments, the third electrode(s) are designed to increase the depth of current penetration in the tissue over the ablation mode so as to increase the thermal damage.

In another method, the third or coagulation electrode is placed in the thermal heating mode at the same time that the active electrode(s) is placed in the ablation mode. In this embodiment, electric current is passed from the coagulation electrode, through the tissue surrounding the hole, to the return electrode at the same time that current is passing between the active and return electrodes. In a specific configuration, this is accomplished by reducing the voltage applied to the coagulation electrode with a passive or active element coupled between the power supply and the coagulation electrode. In this manner, the instrument will immediately begin to coagulate and heat the tissue surrounding the hole as soon as the coagulation electrode enters the hole so that the tissue can close the electric circuit between the coagulation and return electrodes.

In one method, an electrosurgical instrument having an electrode assembly is dipped into electrically conductive fluid such that the conductive fluid is located around and between both active and return electrodes in the electrode assembly. The instrument is then introduced into the patient's mouth to the back of the tongue, and a plurality of holes are formed across the base of the tongue as described above. The instrument is removed from each hole in the thermal heating mode to create thermal damage and to coagulate blood vessels. Typically, the instrument will be dipped into the conductive fluid after being removed from each hole to ensure that sufficient conductive fluid exists for plasma formation and to conduct electric current between the active and return electrodes. This procedure stiffens the base of the tongue, which inhibits the tongue from obstructing breathing as the patient sleeps.

Systems according to the present invention generally include an electrosurgical instrument having a shaft with proximal and distal ends, an electrode assembly at the distal end and one or more connectors coupling the electrode assembly to a source of high frequency electrical energy. The electrode assembly includes one or more active electrode(s) configured for tissue ablation, a return electrode spaced from the active electrode(s) on the instrument shaft and a third, coagulation electrode spaced from the return electrode on the instrument shaft. The system further includes a power source coupled to the electrodes on the instrument shaft for applying a high frequency voltage between the active and return electrodes, and between the coagulation and return electrodes, at the same time. The voltage applied between the coagulation and return electrodes is substantially lower than the voltage applied between the active and return electrodes to allow the former to coagulation severed blood vessels and heat tissue, while the latter ablates tissue.

The active electrode(s) may comprise a single active electrode, or an electrode array, extending from an electrically insulating support member, typically made of an inorganic material such as ceramic, silicone or glass. The active electrode will usually have a smaller exposed surface area than the return and coagulation electrodes such that the current densities are much higher at the active electrode than at the other electrodes. Preferably, the return and coagulation electrodes have relatively large, smooth surfaces extending around the instrument shaft to reduce current densities, thereby minimizing damage to adjacent tissue.

In one embodiment, the system comprises a voltage reduction element coupled between the power source and the coagulation electrode to reduce the voltage applied to the coagulation electrode. The voltage reduction element will typically comprise a passive element, such as a capacitor, resistor, inductor or the like. In the representative embodiment, the power supply will apply a voltage of about 150 to 350 volts rms between the active and return electrodes, and the voltage reduction element will reduce this voltage to about 20 to 90 volts rms to the coagulation electrode. In this manner, the voltage delivered to the coagulation electrode is below the threshold for ablation of tissue, but high enough to coagulation and heat the tissue.

The apparatus may further include a fluid delivery element for delivering electrically conducting fluid to the electrode terminal(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied to the electrode assembly or the target site. In this embodiment, the apparatus may not have a fluid delivery element. In both embodiments, the electrically conducting fluid will preferably generate a current flow path between the electrode terminal(s) and the return electrode(s).

BRIEF DESCRIPTION OF THE DRAWINGS

FIGS. 12A–12D illustrate three embodiments of electrosurgical probes specifically designed for treating obstructive sleep disorders;

DESCRIPTION OF SPECIFIC EMBODIMENTS

Figure 1:
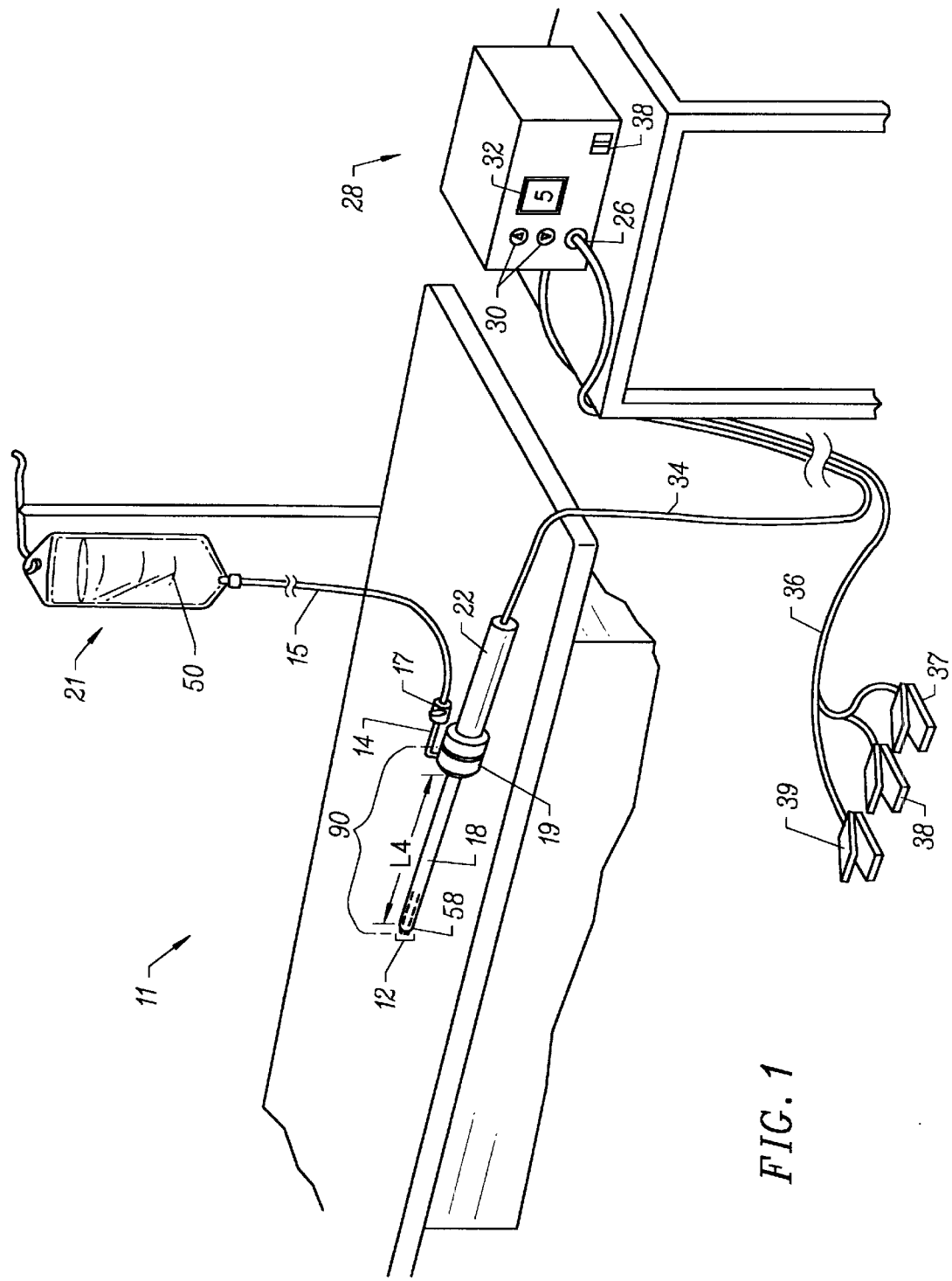
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body, particularly including tissue in the head and neck, such as the ear, mouth, pharynx, larynx, esophagus, nasal cavity and sinuses. These procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue, trachea broncheal strictures and the like. In other procedures, the present invention may be useful for collagen shrinkage, ablation and/or hemostasis in procedures for treating snoring and obstructive sleep apnea (e.g., soft palate, such as the uvula, or tongue/pharynx stiffening, and midline glossectomies), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, myringotomies, tympanostomies or the like.

The present invention is particularly useful for treating snoring and obstructive sleep apnea by creating channels within the tongue, tonsils, palate, or uyula, to stiffen the tissue within these structures. For convenience, the remaining disclosure will be directed specifically to the treatment of obstructive sleep disorders, but it will be appreciated that the system and method can be applied equally well to procedures involving other tissues of the body, as well as to other procedures including open procedures, intravascular procedures, urology, laparascopy, arthroscopy, thoracoscopy or other cardiac procedures, cosmetic surgery, orthopedics, gynecology, otorhinolaryngology, spinal and neurologic procedures, oncology and the like.

In one aspect of the invention, the tissue is volumetrically removed or ablated to form holes, channels, divots or other spaces within the body structure. In this procedure, a high frequency voltage difference is applied between one or more electrode terminal(s) and one or more return electrode(s) to develop high electric field intensities in the vicinity of the target tissue. The high electric field intensities adjacent the electrode terminal(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid or gas, such as isotonic saline, blood or intracellular fluid, delivered to, or already present at, the target site, or a viscous fluid, such as a gel, applied to the target site. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under the conditions described herein, induces the discharge of energetic electrons and photons from the vapor layer and to the surface of the target tissue. This energy may be in the form of energetic photons (e.g., ultraviolet radiation), energetic particles (e.g., electrons or ions) or a combination thereof. A more detailed description of this phenomena, termed Coblation™ can be found in commonly assigned U.S. Pat. No. 5,697,882 the complete disclosure of which is incorporated herein by reference.

Applicant believes that the principle mechanism of tissue removal in the Coblation™ mechanism of the present invention is energetic electrons or ions that have been energized in a plasma adjacent to the electrode terminal(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995). When the density of the vapor layer (or within a bubble formed in the electrically conducting liquid) becomes sufficiently low (i.e., less than approximately 10 20 atoms/cm3 for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating a small of gas and ionizing the gas by driving an electric current through it, or by shining radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

In some embodiments, the present invention applies high frequency (RF) electrical energy in an electrically conducting media environment to remove (i.e., resect, cut or ablate) a tissue structure and to seal transected vessels within the region of the target tissue. The present invention may also be useful for sealing larger arterial vessels, e.g., on the order of about 1 mm in diameter. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter be applied to coagulate with the coagulation electrode(s), and to ablate with the electrode terminal(s). In other embodiments, the power supply is combined with the coagulation instrument such that the coagulation electrode is used when the power supply is in the coagulation mode (low voltage), and the electrode terminal(s) are used when the power supply is in the ablation mode (higher voltage).

In one method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

In some embodiments of the present invention, the tissue is damaged in a thermal heating mode to create necrosed or scarred tissue at the tissue surface. The high frequency voltage in the thermal heating mode is below the threshold of ablation as described above, but sufficient to cause some thermal damage to the tissue immediately surrounding the electrodes without vaporizing or otherwise debulking this tissue. Typically, it is desired to achieve a tissue temperature in the range of about 60° C. to 100° C. to a depth of about 0.2 to 5 mm, usually about 1 to 2 mm. The voltage required for this thermal damage will partly depend on the electrode configurations, the conductivity of the tissue and the area immediately surrounding the electrodes, the time period in which the voltage is applied and the depth of tissue damage desired. With the electrode configurations described in this application (e.g., FIGS. 12–14), the voltage level for thermal heating will usually be in the range of about 20 to 300 volts rms, preferably about 60 to 200 volts rms. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required. If the voltage is too high, however, the surface tissue may be vaporized, debulked or ablated, which is undesirable.

The present invention is also useful for removing or ablating tissue around nerves, such as spinal, peripheral or cranial nerves, e.g., optic nerve, facial nerves, vestibulocochlear nerves and the like. One of the significant drawbacks with the prior art microdebriders, conventional electrosurgical devices and lasers is that these devices do not differentiate between the target tissue and the surrounding nerves or bone. Therefore, the surgeon must be extremely careful during these procedures to avoid damage to the bone or nerves within and around the target site. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode (s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to tissue, will continue to conduct electric current to the return electrode.

This selective ablation or removal of lower impedance tissue in combination with the Coblation™ mechanism of the present invention allows the surgeon to precisely remove tissue around nerves or bone. Applicant has found that the present invention is capable of volumetrically removing tissue closely adjacent to nerves without impairment the function of the nerves, and without significantly damaging the tissue of the epineurium. One of the significant drawbacks with the prior art microdebriders, conventional electrosurgical devices and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately 1020 atoms/cm3 for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break (typically on the order of about 8 eV). Accordingly, the present invention in its current configuration generally does not ablate or remove such fatty tissue. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032,375, filed Feb. 27, 1998, the complete disclosure of which is incorporated herein by reference.

The present invention also provides systems, apparatus and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tissue cells in the tumor through the dissociation or disintegration of organic molecules into non-viable atoms and molecules. Specifically, the present invention converts the solid tissue cells into non-condensable gases that are no longer intact or viable, and thus, not capable of spreading viable tumor particles to other portions of the patient's brain or to the surgical staff. The high frequency voltage is preferably selected to effect controlled removal of these tissue cells while minimizing substantial tissue necrosis to surrounding or underlying tissue. A more complete description of this phenomena can be found in co-pending U.S. patent application Ser. No. 09/109, 219, filed Jun. 30, 1998, the complete disclosure of which is incorporated herein by reference.

In other procedures, e.g., soft palate or tongue/pharynx stiffening, it may be desired to shrink or contract collagen connective tissue at the target site. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980). Consequently, the controlled heating of tissue to a precise depth is critical to the achievement of therapeutic collagen shrinkage. A more detailed description of collagen shrinkage can be found in U.S. patent application Ser. No. 08/942,580 filed on Oct. 2, 1997.

The preferred depth of heating to effect the shrinkage of collagen in the heated region (i.e., the depth to which the tissue is elevated to temperatures between 60° C. to 70° C.) generally depends on (1) the thickness of the tissue, (2) the location of nearby structures (e.g., nerves) that should not be exposed to damaging temperatures, and/or (3) the location of the collagen tissue layer within which therapeutic shrinkage is to be effected. The depth of heating is usually in the range from 0 to 3.5 mm. In the case of collagen within the soft palate or uvula, the depth of heating is preferably in the range from about 0.5 to about 3.5 mm.

The electrosurgical instrument will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

For procedures within the mouth and throat, the shaft will have a suitable diameter and length to allow the surgeon to reach the target by delivering the instrument shaft through the patient's mouth or another opening. Thus, the shaft will usually have a length in the range of about 5–25 cm, and a diameter in the range of about 0.5 to 5 mm. For channeling procedures or other procedures requiring the formation of holes, channels or other spaces, the distal end portion of the shaft will usually have a diameter less than 3 mm, preferably less than about 1.0 mm. For procedures in the lower throat, such as laryngectomies, vocal cord papillomas or spasmodic dysphorias, the shaft will be suitably designed to access the larynx. For example, the shaft may be flexible, or have a distal bend to accommodate the bend in the patient's throat. In this regard, the shaft may be a rigid shaft having a specifically designed bend to correspond with the geometry of the mouth and throat, or it may have a flexible distal end, or it may be part of a catheter. In any of these embodiments, the shaft may also be introduced through rigid or flexible endoscopes.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter. Specific shaft designs will be described in detail in connection with the figures hereinafter.

The electrode terminal(s) are preferably supported within or by an inorganic insulating support positioned near the distal end of the instrument shaft. The return electrode may be located on the instrument shaft, on another instrument or on the external surface of the patient (i.e., a dispersive pad). The close proximity of nerves and other sensitive tissue in the mouth and throat, however, makes a bipolar design more preferable because this minimizes the current flow through non-target tissue and surrounding nerves. Accordingly, the return electrode is preferably either integrated with the instrument body, or another instrument located in close proximity thereto. The proximal end of the instrument(s) will include the appropriate electrical connections for coupling the return electrode(s) and the electrode terminal(s) to a high frequency power supply, such as an electrosurgical generator.

The return electrode is typically spaced proximally from the active electrode(s) a suitable distance to avoid electrical shorting between the active and return electrodes in the presence of electrically conductive fluid. In the embodiments described herein, the distal edge of the exposed surface of the return electrode is spaced about 0.5 to 25 mm from proximal edge of the exposed surface of the active electrode(s), preferably about 1.0 to 5.0 mm. Of course, this distance may vary with different voltage ranges, conductive fluids, and depending on the proximity of tissue structures to active and return electrodes. The return electrode will typically have an exposed length in the range of about 1 to 20 mm.

The current flow path between the electrode terminals and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, hypotonic saline or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood or intracellular saline, may be sufficient to establish a conductive path between the return electrode(s) and the electrode terminal (s), and to provide the conditions for establishing a vapor layer, as described above. However, conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal (s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

In some procedures, it may also be necessary to retrieve or aspirate the electrically conductive fluid and/or the non-condensible gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode (s) can be found in commonly assigned, co-pending patent application Ser. No. 09/010,382, filed Jan. 21, 1998, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation products do not flow through the patient's vasculature or into other portions of the body. In addition, it may be desirable to limit the amount of suction to limit the undesirable effect suction may have on hemostasis of severed blood vessels.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be more precisely controlled, for example, by the use of a multiplicity of small electrode terminals whose effective diameters or principal dimensions range from about 10 mm to 0.01 mm, preferably from about 2 mm to 0.05 mm, and more preferably from about 1 mm to 0.1 mm. In this embodiment, electrode areas for both circular and non-circular terminals will have a contact area (per electrode terminal) below 50 mm2 for electrode arrays and as large as 75 mm2 for single electrode embodiments. In multiple electrode arrays, the contact area of each electrode terminal is typically in the range from 0.0001 mm2 to 1 mm2, and more preferably from 0.001 mm2 to 0.5 mm2. The circumscribed area of the electrode array or electrode terminal is in the range from 0.25 mm2 to 75 mm2, preferably from 0.5 mm2 to 40 mm2. In multiple electrode embodiments, the array will usually include at least two isolated electrode terminals, often at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor layer and subsequent plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

In other embodiments, the active electrodes are spaced from the tissue a sufficient distance to minimize or avoid contact between the tissue and the vapor layer formed around the active electrodes. In these embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the tissue bonds are dissociated or broken as in previous embodiments, while minimizing the electron flow, and thus the thermal energy, in contact with the tissue.

The electrically conducting fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Applicant has found that a more conductive fluid, or one with a higher ionic concentration, will usually provide a more aggressive ablation rate. For example, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals near the left end of the periodic chart. In addition, other electronegative elements may be used in place of chlorine, such as fluorine.

The voltage difference applied between the return electrode(s) and the electrode terminal(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400–600 kHz) to minimize low frequency current flow into the heart or the nerves of the head and neck. The RMS (root mean square) voltage applied will usually be in the range from about 5 volts to 1000 volts, preferably being in the range from about 10 volts to 500 volts, often between about 150 to 400 volts depending on the electrode terminal size, the operating frequency and the operation mode of the particular procedure or desired effect on the tissue (i.e., contraction, coagulation, cutting or ablation). Typically, the peak-to-peak voltage for ablation or cutting with a square wave form will be in the range of 10 to 2000 volts and preferably in the range of 100 to 1800 volts and more preferably in the range of about 300 to 1500 volts, often in the range of about 300 to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 to 600 kHz may be used in certain procedures in which stray low frequency currents may be problematic. A description of one suitable power source can be found in co-pending patent applications Ser. Nos. 09/058,571 and 09/058,336, filed Apr. 10, 1998, the complete disclosure of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In one embodiment, an electrosurgical catheter or probe comprises a single active electrode terminal that extends from an insulating member, e.g., ceramic, at the distal end of the shaft. The insulating member is preferably a tubular structure that separates the active electrode terminal from a tubular or annular return electrode positioned proximal to the insulating member and the active electrode. In another embodiment, the catheter or probe includes a single active electrode that can be rotated relative to the rest of the catheter body, or the entire catheter may be rotated related to the lead. The single active electrode can be positioned adjacent the abnormal tissue and energized and rotated as appropriate to remove this tissue.

The current flow path between the electrode terminal(s) and the return electrode(s) may be generated by submerging the tissue site in an electrical conducting media (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode.

Referring to FIG. 1, an exemplary electrosurgical system 11 for treatment of tissue in the head and neck will now be described in detail. Electrosurgical system 11 generally comprises an electrosurgical handpiece or probe 90 connected to a power supply 28 for providing high frequency voltage to a target site and a fluid source 21 for supplying electrically conducting fluid 50 to probe 90. In addition, electrosurgical system 11 may include an endoscope (not shown) with a fiber optic head light for viewing the surgical site, particularly in sinus procedures or procedures in the ear or the back of the mouth. The endoscope may be integral with probe 90, or it may be part of a separate instrument. The system 11 may also include a vacuum source (not shown) for coupling to a suction lumen or tube 205 (see FIG. 2) in the probe 90 for aspirating the target site.

As shown, probe 90 generally includes a proximal handle 19 and an elongate shaft 18 having an array 12 of electrode terminals 58 at its distal end. A connecting cable 34 has a connector 26 for electrically coupling the electrode terminals 58 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 14 of probe 90 for supplying electrically conducting fluid 50 to the target site. Fluid supply tube 15 may be connected to a suitable pump (not shown), if desired.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into the "sub-ablation" mode (e.g., coagulation or contraction of tissue). The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 28 applies a low enough voltage to the electrode terminals to avoid vaporization of the electrically conductive fluid and subsequent molecular dissociation of the tissue. The surgeon may automatically toggle the power supply between the ablation and sub-ablation modes by alternatively stepping on foot pedals 37, 38, respectively. In some embodiments, this allows the surgeon to quickly move between coagulation/thermal heating and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in U.S. Provisional Patent Application No. 60/062,997, filed Oct. 23, 1997 previously incorporated herein by reference.

Figure 22:
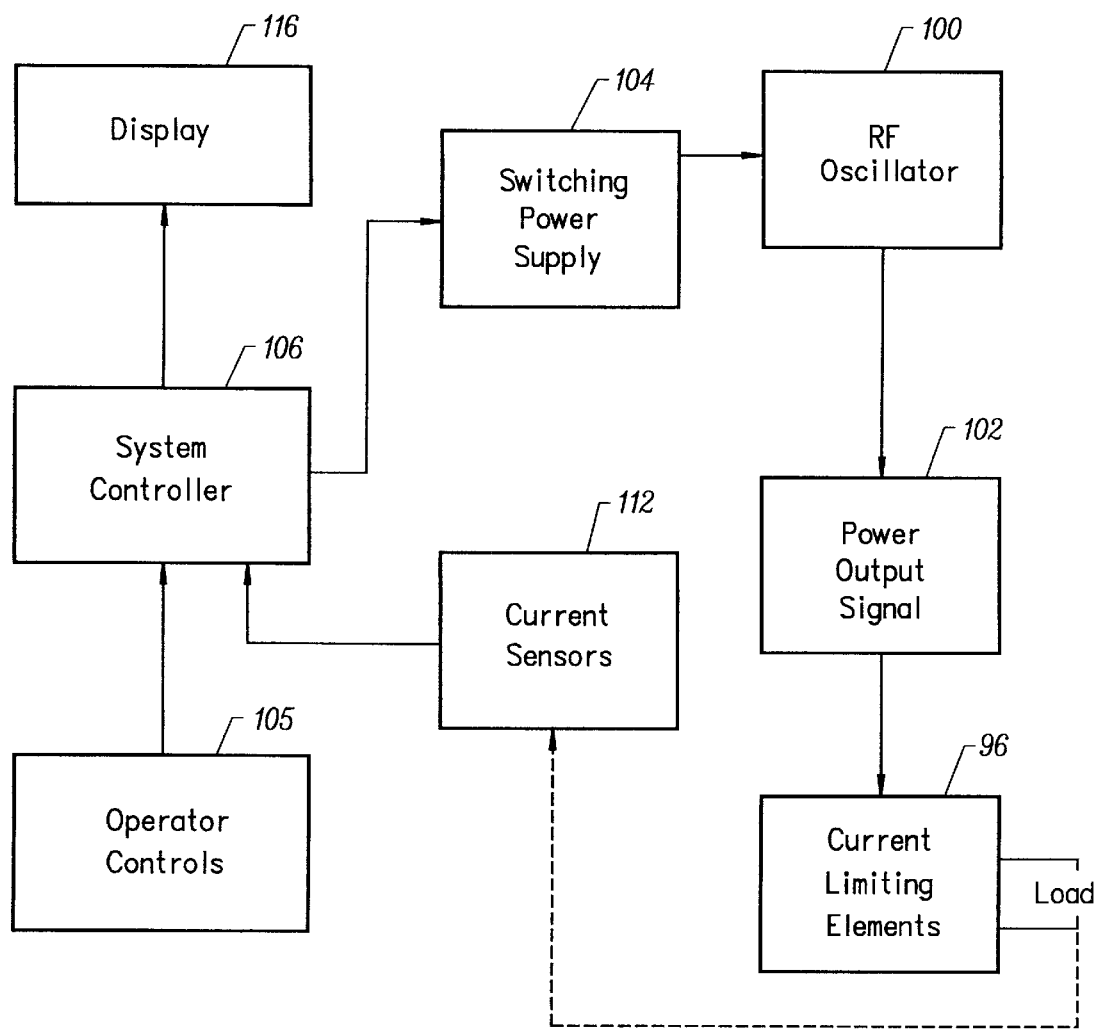
FIG. 22 schematically illustrates one embodiment of a power supply according to the present invention.
Figure 23:
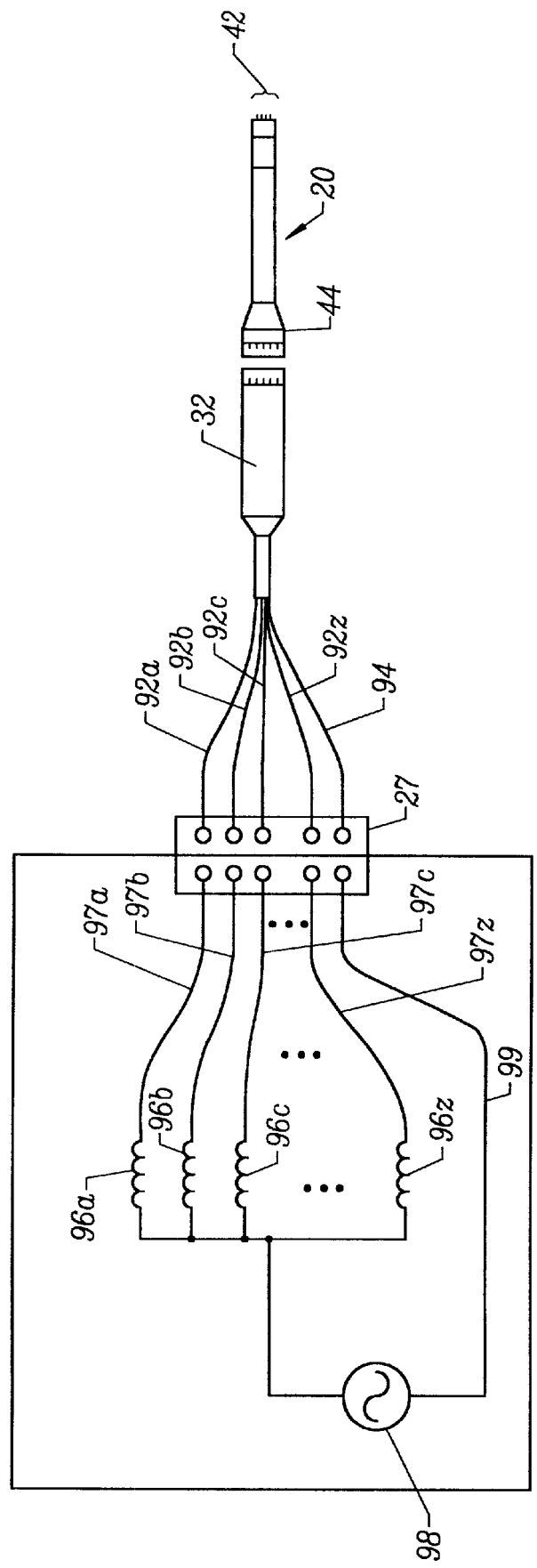
FIG. 23 illustrates an electrosurgical system incorporating a plurality of active electrodes and associated current limiting elements.

Referring now to FIGS. 22 and 23, a representative high frequency power supply for use according to the principles of the present invention will now be described. The high frequency power supply of the present invention is configured to apply a high frequency voltage of about 10 to 500 volts RMS between one or more electrode terminals (and/or coagulation electrode) and one or more return electrodes. In the exemplary embodiment, the power supply applies about 70–350 volts RMS in the ablation mode and about 20 to 90 volts in a subablation mode, preferably 45 to 70 volts in the subablation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular procedure, e.g., arthroscopic surgery, dermatological procedure, ophthalmic procedures, open surgery or other endoscopic surgery procedure.

As shown in FIG. 22, the power supply generally comprises a radio frequency (RF) power oscillator 100 having output connections for coupling via a power output signal 102 to the load impedance, which is represented by the electrode assembly when the electrosurgical probe is in use. In the representative embodiment, the RF oscillator operates at about 100 kHz. The RF oscillator is not limited to this frequency and may operate at frequencies of about 300 kHz to 600 kHz. In particular, for cardiac applications, the RF oscillator will preferably operate in the range of about 400 kHz to about 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 102 is designed to incur minimal voltage decrease (i.e., sag) under load. This improves the applied voltage to the electrode terminals and the return electrode, which improves the rate of volumetric removal (ablation) of tissue.

Power is supplied to the oscillator 100 by a switching power supply 104 coupled between the power line and the RF oscillator rather than a conventional transformer. The switching power supply 104 allows the generator to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 104 operates at about 100 kHz.

A controller 106 coupled to the operator controls 105 (i.e., foot pedals and voltage selector) and display 116, is connected to a control input of the switching power supply 104 for adjusting the generator output power by supply voltage variation. The controller 106 may be a microprocessor or an integrated circuit. The power supply may also include one or more current sensors 112 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield", thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries, usually about 300 microhenries, for each of the channels supplying current to the electrode terminals 02 (see FIG. 2).

Alternatively, in one embodiment, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel). Power output signal may also be coupled to a plurality of current limiting elements 96, which are preferably located on the daughter board since the current limiting elements may vary depending on the application.

Figure 2:
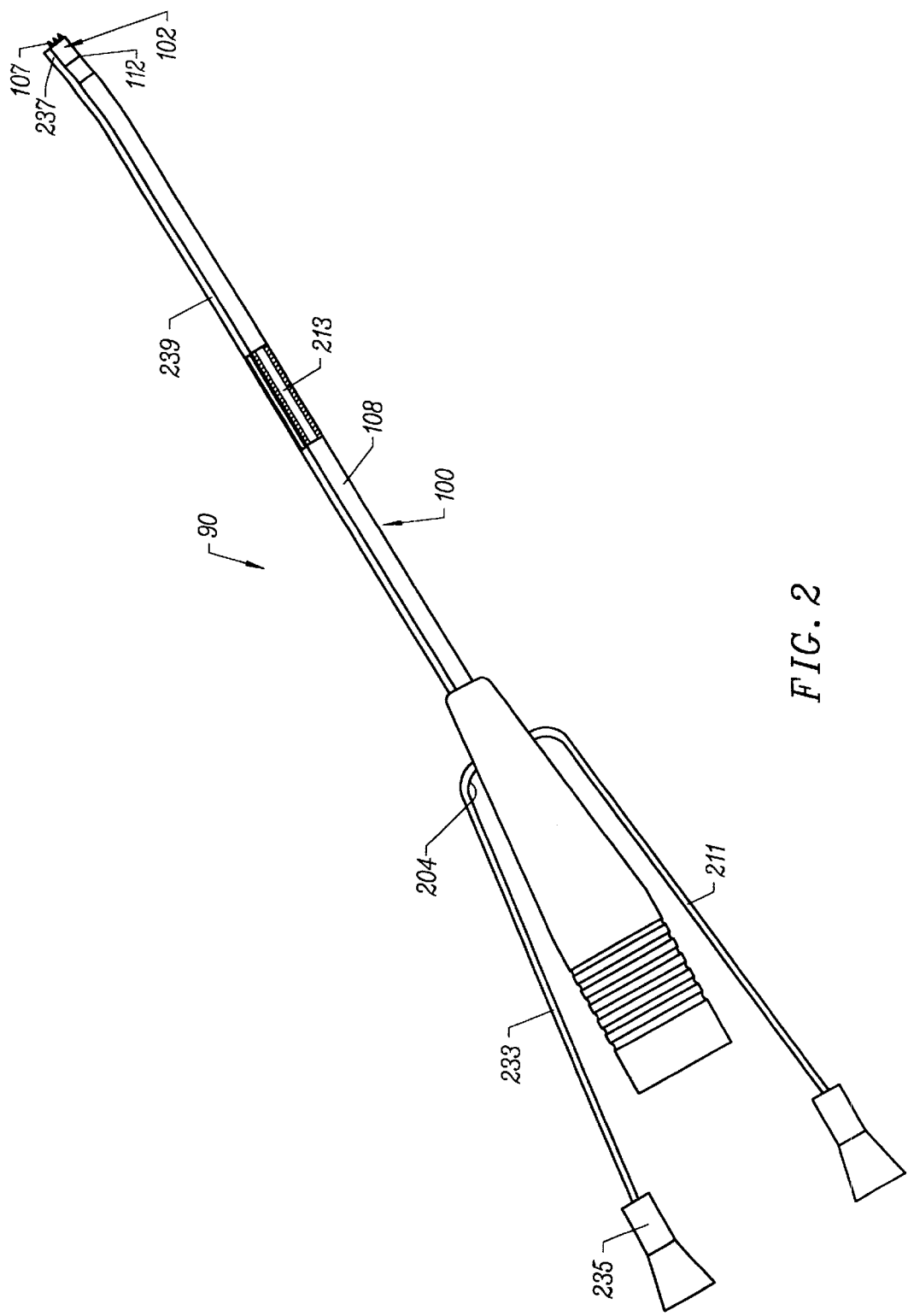
FIG. 2 is a side view of an electrosurgical probe according to the present invention.
Figure 3:
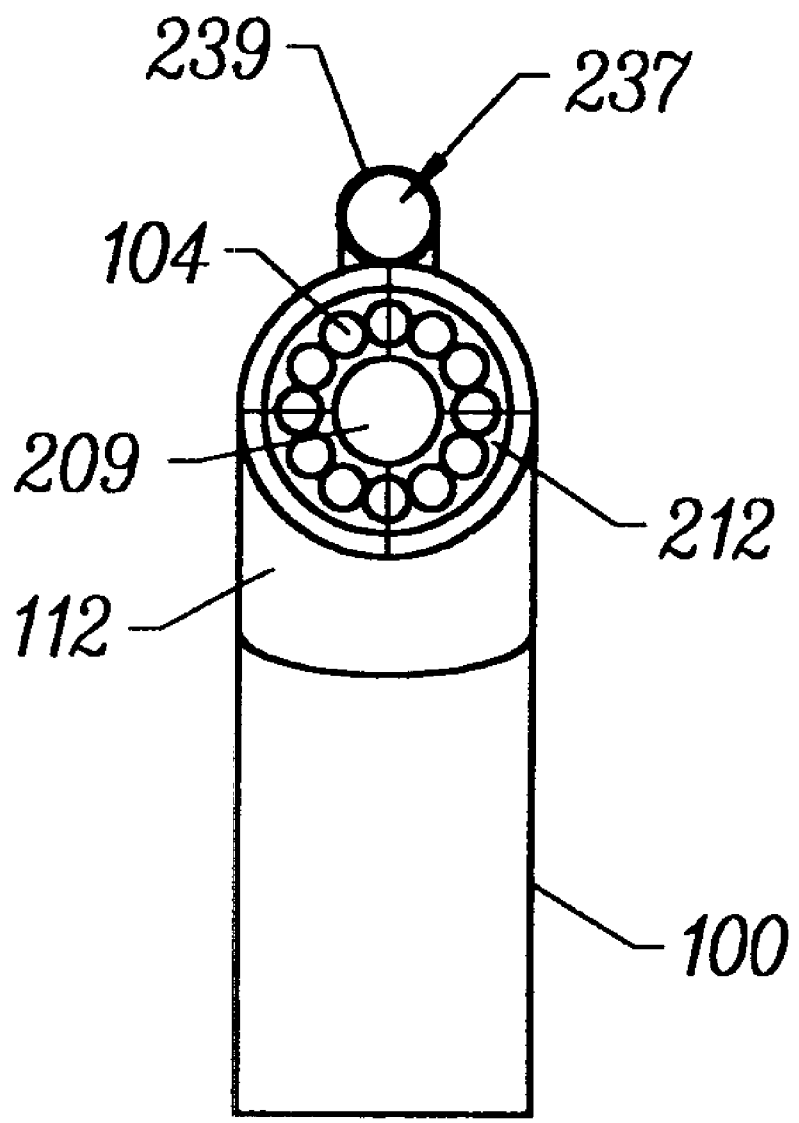
FIG. 3 is an end view of the probe of FIG. 2.
Figure 4:
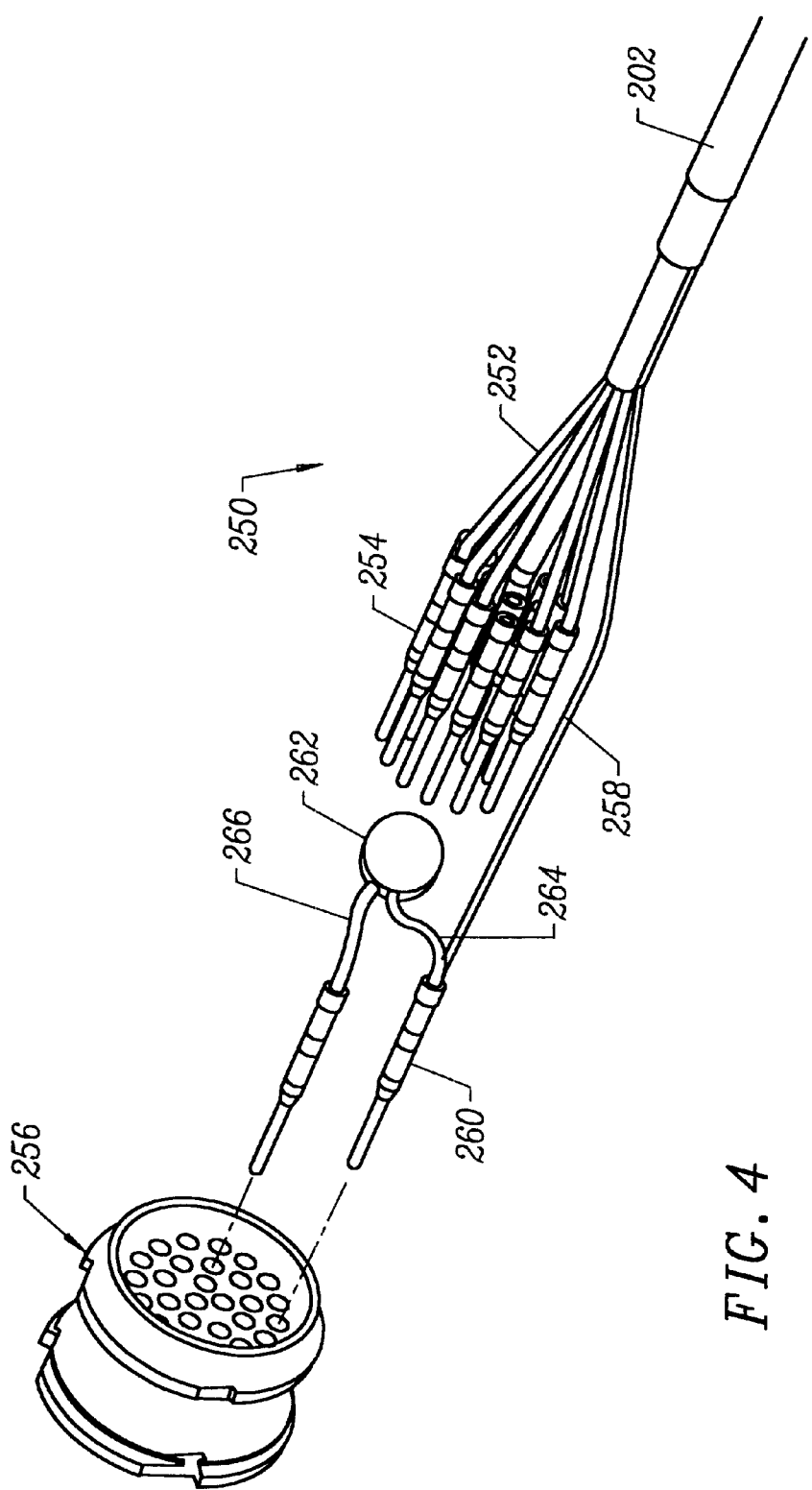
FIG. 4 is a cross sectional view of the electrosurgical probe of FIG. 1.

FIGS. 2–4 illustrate an exemplary electrosurgical probe 90 constructed according to the principles of the present invention. As shown in FIG. 2, probe 90 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 204 typically comprises a plastic material that is easily molded into a suitable shape for handling by the surgeon. Handle 204 defines an inner cavity (not shown) that houses the electrical connections 250 (FIG. 4), and provides a suitable interface for connection to an electrical connecting cable 22 (see FIG. 1). Electrode support member 102 extends from the distal end of shaft 100 (usually about 1 to 20 mm), and provides support for a plurality of electrically isolated electrode terminals 104 (see FIG. 3). As shown in FIG. 2, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, fluid tube 239 is a peek tubing that extends along the exterior of shaft 100 to a point just distal of return electrode 112 (see FIG. 3). In this embodiment, the fluid is directed through an opening 237 past return electrode 112 to the electrode terminals 104. Probe 90 may also include a valve 17 (FIG. 1) or equivalent structure for controlling the flow rate of the electrically conducting fluid to the target site.

As shown in FIG. 2, the distal portion of shaft 100 is preferably bent to improve access to the operative site of the tissue being treated. Electrode support member 102 has a substantially planar tissue treatment surface 212 (FIG. 3) that is usually at an angle of about 10 to 90 degrees relative to the longitudinal axis of shaft 100, preferably about 30 to 60 degrees and more preferably about 45 degrees. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in U.S. Pat. No. 5,697,909, the complete disclosure of which has previously been incorporated herein by reference.

In the embodiment shown in FIGS. 2–4, probe 90 includes a return electrode 112 for completing the current path between electrode terminals 104 and a high frequency power supply 28 (see FIG. 1). As shown, return electrode 112 preferably comprises an exposed portion of shaft 100 shaped as an annular conductive band near the distal end of shaft 100 slightly proximal to tissue treatment surface 212 of electrode support member 102, typically about 0.5 to 10 mm and more preferably about 1 to 10 mm. Return electrode 112 or shaft 100 is coupled to a connector 258 that extends to the proximal end of probe 90, where it is suitably connected to power supply 28 (FIG. 1).

As shown in FIG. 2, return electrode 112 is not directly connected to electrode terminals 104. To complete this current path so that electrode terminals 104 are electrically connected to return electrode 112, electrically conducting fluid (e.g., isotonic saline) is caused to flow therebetween. In the representative embodiment, the electrically conducting fluid is delivered through fluid tube 233 to opening 237, as described above. Alternatively, the fluid may be delivered by a fluid delivery element (not shown) that is separate from probe 90. In arthroscopic surgery, for example, the body cavity will be flooded with isotonic saline and the probe 90 will be introduced into this flooded cavity. Electrically conducting fluid will be continually resupplied to maintain the conduction path between return electrode 112 and electrode terminals 104. In other embodiments, the distal portion of probe 90 may be dipped into a source of electrically conductive fluid, such as a gel or isotonic saline, prior to positioning at the target site. Applicant has found that surface tension of the fluid and/or the viscous nature of a gel allows the conductive fluid to remain around the active and return electrodes for long enough to complete its function according to the present invention, as described below. Alternatively, the conductive fluid, such as a gel, may be applied directly to the target site.

Figure 5:
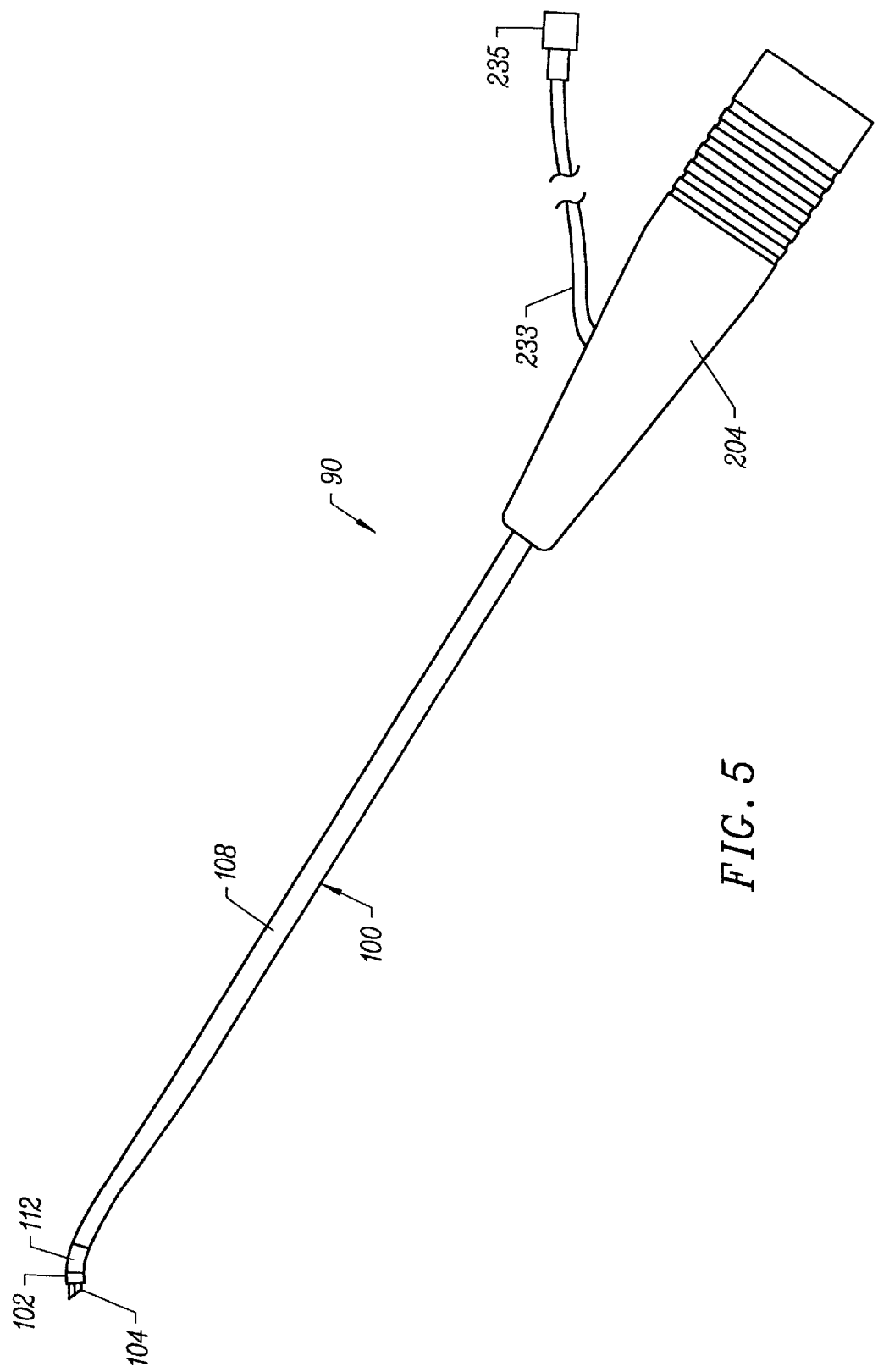
FIG. 5 is an exploded view of a proximal portion of the electrosurgical probe.

In alternative embodiments, the fluid path may be formed in probe 90 by, for example, an inner lumen or an annular gap between the return electrode and a tubular support member within shaft 100 (see FIG. 5). This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 90 via a fluid supply tube (not shown) that may or may not have a controllable valve. A more complete description of an electrosurgical probe incorporating one or more fluid lumen(s) can be found in U.S. Pat. No. 5,697,281, the complete disclosure of which has previously been incorporated herein by reference.

Referring to FIG. 3, the electrically isolated electrode terminals 104 are spaced apart over tissue treatment surface 212 of electrode support member 102. The tissue treatment surface and individual electrode terminals 104 will usually have dimensions within the ranges set forth above. In the representative embodiment, the tissue treatment surface 212 has a circular cross-sectional shape with a diameter in the range of 1 mm to 20. The individual electrode terminals 104 preferably extend outward from tissue treatment surface 212 by a distance of about 0.1 to 4 mm, usually about 0.2 to 2 mm. Applicant has found that this configuration increases the high electric field intensities and associated current densities around electrode terminals 104 to facilitate the ablation of tissue as described in detail above.

In the embodiment of FIGS. 2–4, the probe includes a single, larger opening 209 in the center of tissue treatment surface 212, and a plurality of electrode terminals (e.g., about 3–15) around the perimeter of surface 212 (see FIG. 3). Alternatively, the probe may include a single, annular, or partially annular, electrode terminal at the perimeter of the tissue treatment surface. The central opening 209 is coupled to a suction lumen (not shown) within shaft 100 and a suction tube 211 (FIG. 2) for aspirating tissue, fluids and/or gases from the target site. In this embodiment, the electrically conductive fluid generally flows radially inward past electrode terminals 104 and then back through the opening 209. Aspirating the electrically conductive fluid during surgery allows the surgeon to see the target site, and it prevents the fluid from flowing into the patient's body, e.g., through the sinus passages, down the patient's throat or into the ear canal.

Figure 6:
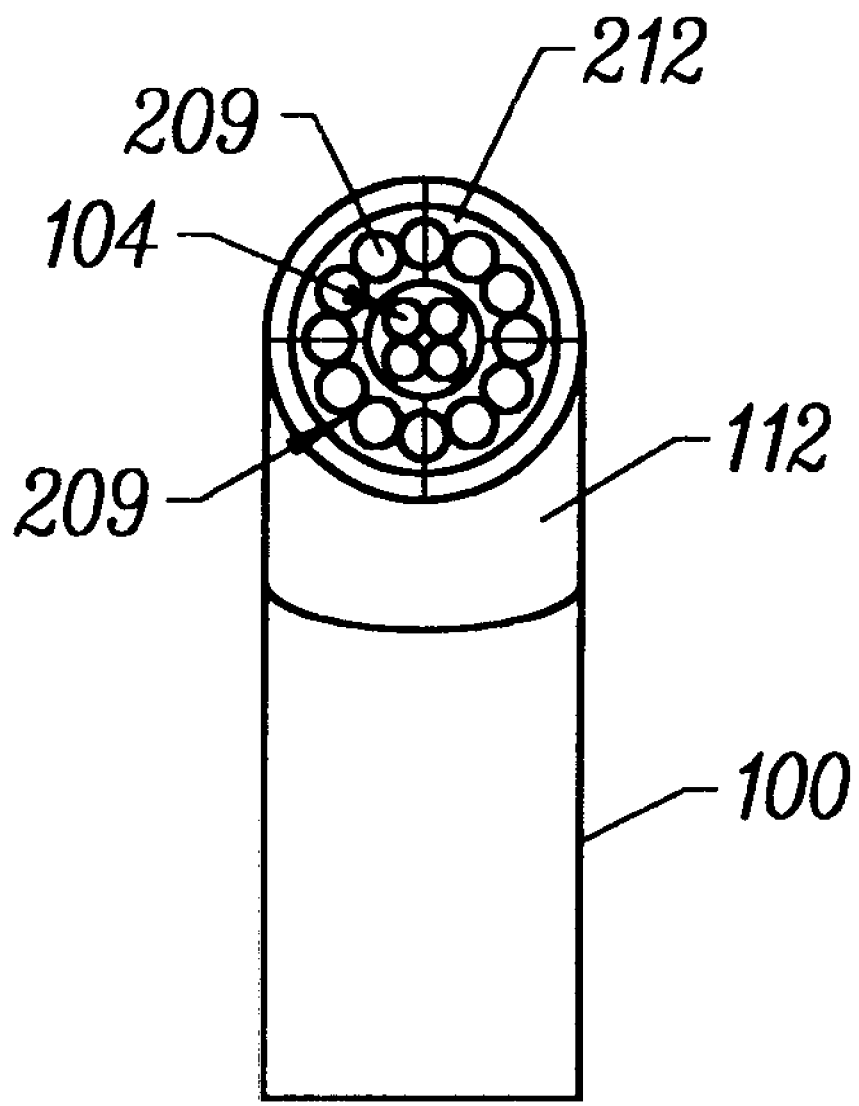
FIG. 6 is an end view of an alternative electrosurgical probe incorporating an inner fluid lumen.

Of course, it will be recognized that the distal tip of probe may have a variety of different configurations. For example, the probe may include a plurality of openings 209 around the outer perimeter of tissue treatment surface 212 (see FIG. 6). In this embodiment, the electrode terminals 104 extend from the center of tissue treatment surface 212 radially inward from openings 209. The openings are suitably coupled to fluid tube 233 for delivering electrically conductive fluid to the target site, and suction tube 211 for aspirating the fluid after it has completed the conductive path between the return electrode 112 and the electrode terminals 104.

FIG. 4 illustrates the electrical connections 250 within handle 204 for coupling electrode terminals 104 and return electrode 112 to the power supply 28. As shown, a plurality of wires 252 extend through shaft 100 to couple terminals 104 to a plurality of pins 254, which are plugged into a connector block 256 for coupling to a connecting cable 22 (FIG. 1). Similarly, return electrode 112 is coupled to connector block 256 via a wire 258 and a plug 260.

According to the present invention, the probe 90 further includes an identification element that is characteristic of the particular electrode assembly so that the same power supply 28 can be used for different electrosurgical operations. In one embodiment, for example, the probe 90 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. The voltage reduction element primarily allows the electrosurgical probe 90 to be compatible with other ArthroCare generators that are adapted to apply higher voltages for ablation or vaporization of tissue. For thermal heating or coagulation of tissue, for example, the voltage reduction element will serve to reduce a voltage of about 100 to 170 volts rms (which is a setting of 1 or 2 on the ArthroCare Model 970 and 980 (i.e., 2000) Generators) to about 45 to 60 volts rms, which is a suitable voltage for coagulation of tissue without ablation (e.g., molecular dissociation) of the tissue.

Of course, for some procedures, such as endoscopic sinus surgery, the probe will typically not require a voltage reduction element. Alternatively, the probe may include a voltage increasing element or circuit, if desired. Alternatively or additionally, the cable 22 that couples the power supply 28 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor. Further, it should be noted that the present invention can be used with a power supply that is adapted to apply a voltage within the selected range for treatment of tissue. In this embodiment, a voltage reduction element or circuitry may not be desired.

Figure 7A:
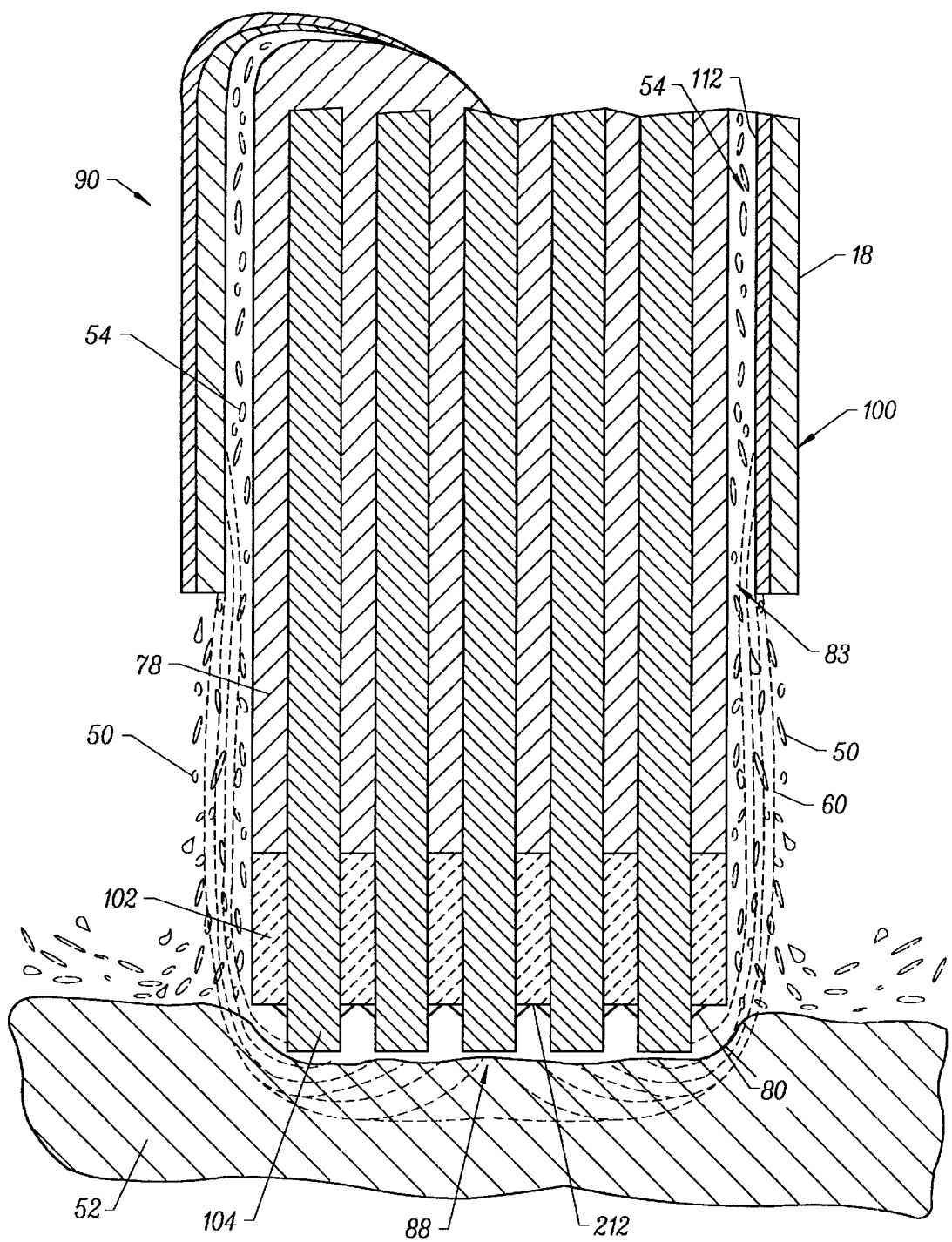
FIGS. 7A–7C are cross-sectional views of the distal portions of three different embodiments of an electrosurgical probe according to the present invention.
Figure 7B:
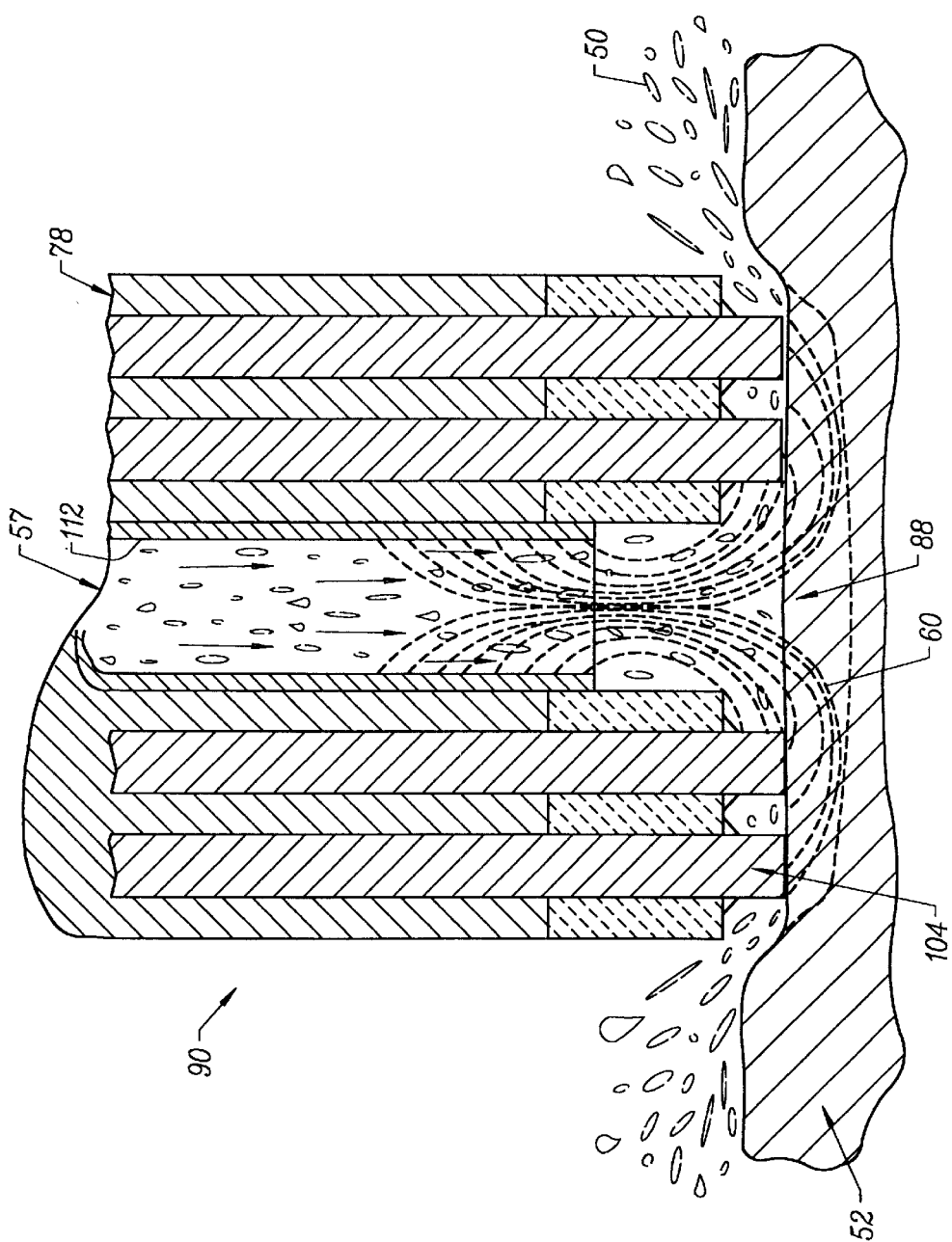
Figure 7C:
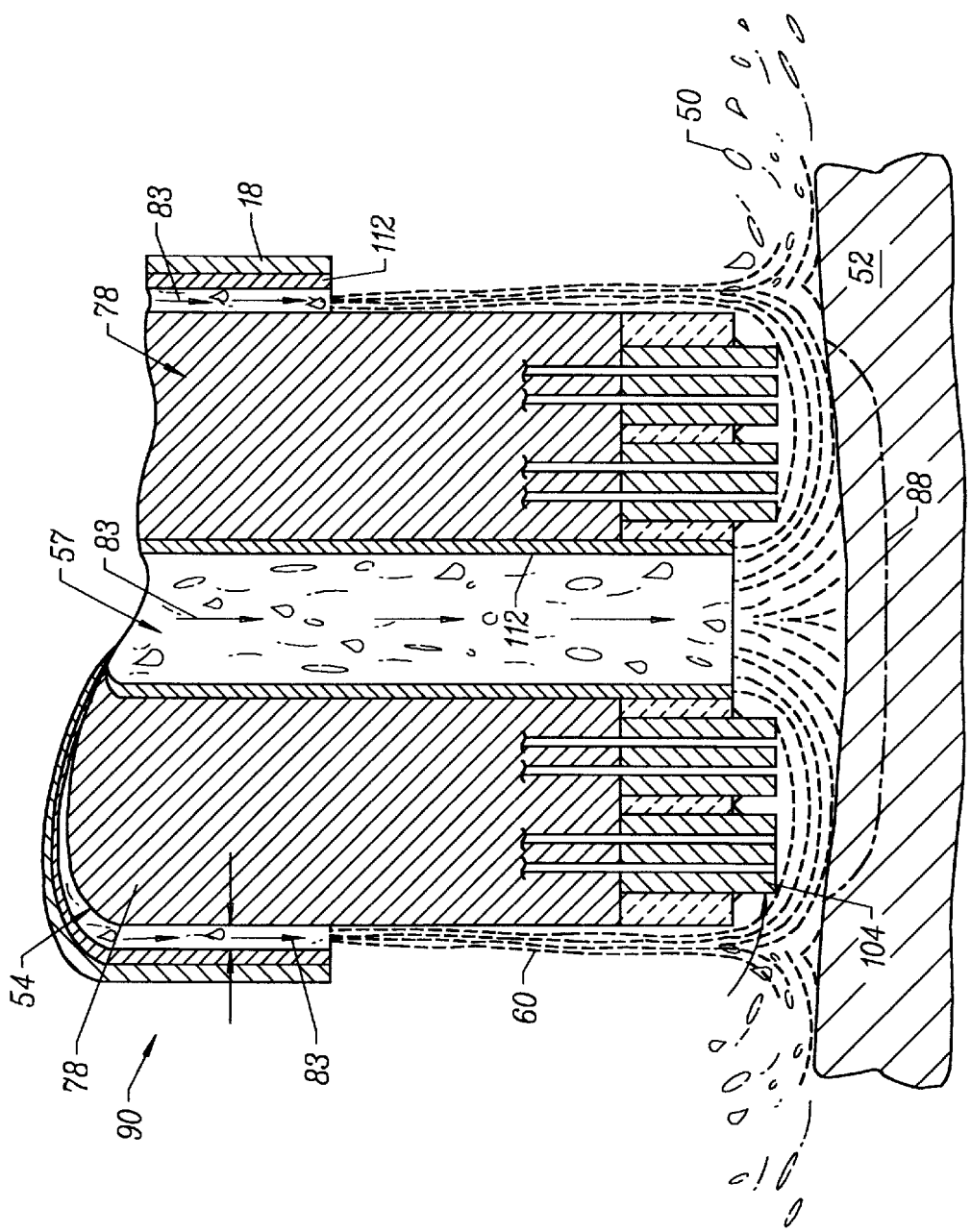

FIGS. 7A–7C schematically illustrate the distal portion of three different embodiments of probe 90 according to the present invention. As shown in 7A, electrode terminals 104 are anchored in a support matrix 102 of suitable insulating material (e.g., ceramic or glass material, such as alumina, zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support matrix 102 is adhesively joined to a tubular support member 78 that extends most or all of the distance between matrix 102 and the proximal end of probe 90. Tubular member 78 preferably comprises an electrically insulating material, such as an epoxy or silicone-based material.

In a preferred construction technique, electrode terminals 104 extend through pre-formed openings in the support matrix 102 so that they protrude above tissue treatment surface 212 by the desired distance. The electrodes are then bonded to the tissue treatment surface 212 of support matrix 102, typically by an inorganic sealing material 80. Sealing material 80 is selected to provide effective electrical insulation, and good adhesion to both the alumina matrix 102 and the platinum or titanium electrode terminals. Sealing material 80 additionally should have a compatible thermal expansion coefficient and a melting point well below that of platinum or titanium and alumina or zirconia, typically being a glass or glass ceramic.

In the embodiment shown in FIG. 7A, return electrode 112 comprises an annular member positioned around the exterior of shaft 100 of probe 90. Return electrode 90 may fully or partially circumscribe tubular support member 78 to form an annular gap 54 therebetween for flow of electrically conducting liquid 50 therethrough, as discussed below. Gap 54 preferably has a width in the range of 0.25 mm to 4 mm. Alternatively, probe may include a plurality of longitudinal ribs between support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 112 prevents direct electrical contact between return electrode 56 and any adjacent body structure. Such direct electrical contact between a body structure (e.g., tendon) and an exposed electrode member 112 could result in unwanted heating and necrosis of the structure at the point of contact causing necrosis.

As shown in FIG. 7A, return electrode 112 is not directly connected to electrode terminals 104. To complete this current path so that terminals 104 are electrically connected to return electrode 112, electrically conducting liquid 50 (e.g:, isotonic saline) is caused to flow along fluid path(s) 83. Fluid path 83 is formed by annular gap 54 between outer return electrode 112 and tubular support member. The electrically conducting liquid 50 flowing through fluid path 83 provides a pathway for electrical current flow between electrode terminals 104 and return electrode 112, as illustrated by the current flux lines 60 in FIG. 6A. When a voltage difference is applied between electrode terminals 104 and return electrode 112, high electric field intensities will be generated at the distal tips of terminals 104 with current flow from terminals 104 through the target tissue to the return electrode, the high electric field intensities causing ablation of tissue 52 in zone 88.

FIG. 7B illustrates another alternative embodiment of electrosurgical probe 90 which has a return electrode 112 positioned within tubular member 78. Return electrode 112 is preferably a tubular member defining an inner lumen 57 for allowing electrically conducting liquid 50 (e.g., isotonic saline) to flow therethrough in electrical contact with return electrode 112. In this embodiment, a voltage difference is applied between electrode terminals 104 and return electrode 112 resulting in electrical current flow through the electrically conducting liquid 50 as shown by current flux lines 60 (FIG. 3). As a result of the applied voltage difference and concomitant high electric field intensities at the tips of electrode terminals 104, tissue 52 becomes ablated or transected in zone 88.

FIG. 7C illustrates another embodiment of probe 90 that is a combination of the embodiments in FIGS. 7A and 7B. As shown, this probe includes both an inner lumen 57 and an outer gap or plurality of outer lumens 54 for flow of electrically conductive fluid. In this embodiment, the return electrode 112 may be positioned within tubular member 78 as in FIG. 7B, outside of tubular member 78 as in FIG. 7A, or in both locations.

Figure 9:
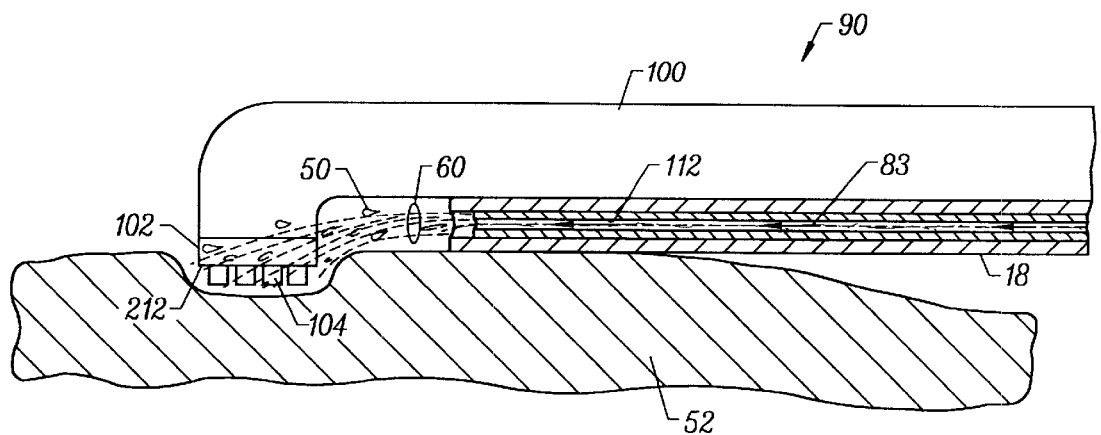
FIG. 9 illustrates an electrosurgical probe with a 90° distal bend and a lateral fluid lumen.

FIG. 9 illustrates another embodiment of probe 90 where the distal portion of shaft 100 is bent so that electrode terminals extend transversely to the shaft. Preferably, the distal portion of shaft 100 is perpendicular to the rest of the shaft so that tissue treatment surface 212 is generally parallel to the shaft axis. In this embodiment, return electrode 112 is mounted to the outer surface of shaft 100 and is covered with an electrically insulating jacket 18. The electrically conducting fluid 50 flows along flow path 83 through return electrode 112 and exits the distal end of electrode 112 at a point proximal of tissue treatment surface 212. The fluid is directed exterior of shaft to surface 212 to create a return current path from electrode terminals 104, through the fluid 50, to return electrode 112, as shown by current flux lines 60.

Figure 10:
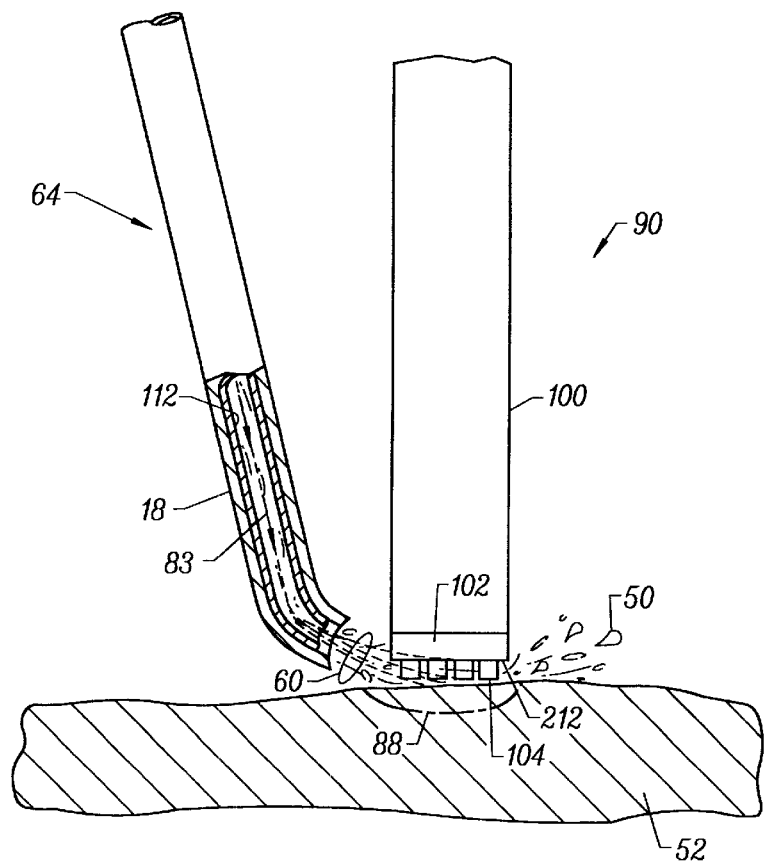
FIG. 10 illustrates an electrosurgical system with a separate fluid delivery instrument according to the present invention.

FIG. 10 illustrates another embodiment of the invention where electrosurgical system 11 further includes a liquid supply instrument 64 for supplying electrically conducting fluid 50 between electrode terminals 104 and return electrode 112. Liquid supply instrument 64 comprises an inner tubular member or return electrode 112 surrounded by an electrically insulating jacket 18. Return electrode 112 defines an inner passage 83 for flow of fluid 50. As shown in FIG. 8, the distal portion of instrument 64 is preferably bent so that liquid 50 is discharged at an angle with respect to instrument 64. This allows the surgical team to position liquid supply instrument 64 adjacent tissue treatment surface 212 with the proximal portion of supply instrument 64 oriented at a similar angle to probe 90.

Figure 8A:
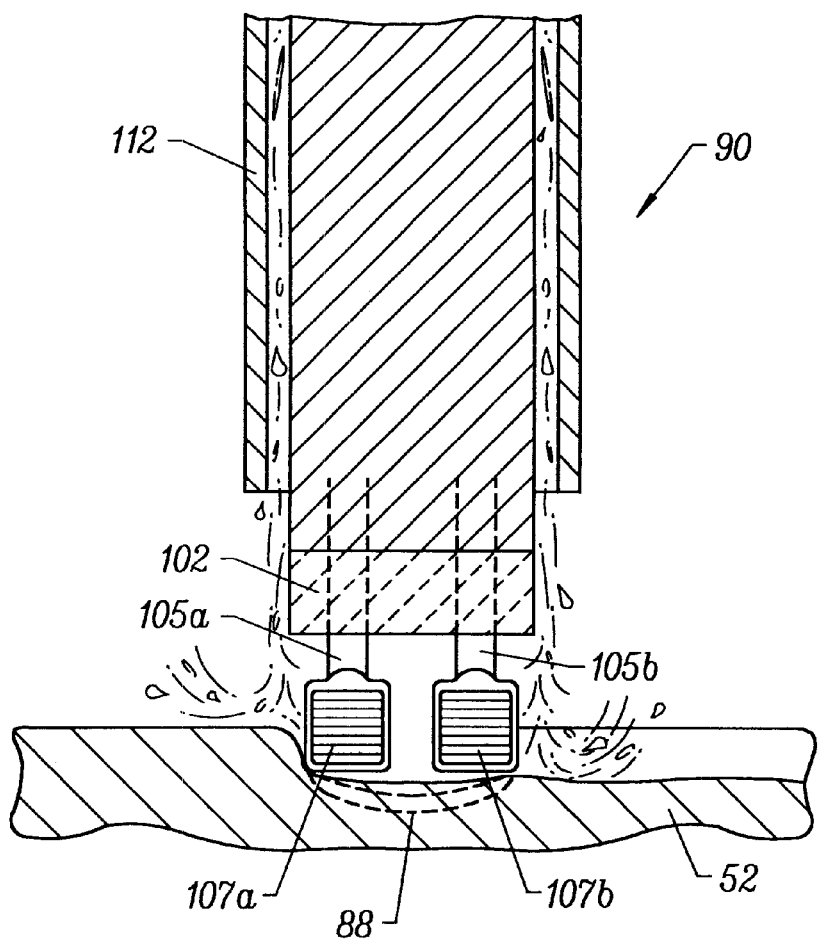
FIGS. 8A and 8B are cross-sectional and end views, respectively, of yet another electrosurgical probe incorporating flattened electrode terminals.
Figure 8B:
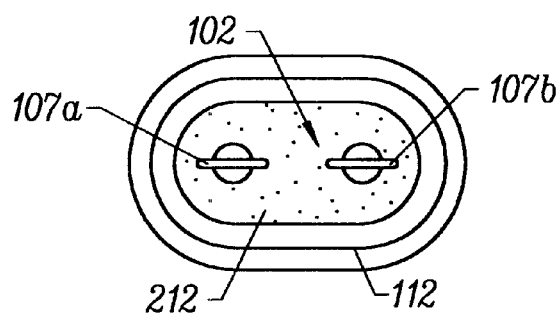

The present invention is not limited to an electrode array disposed on a relatively planar surface at the distal tip of probe 90, as described above. Referring to FIGS. 8A and 8B, an alternative probe 90 includes a pair of electrodes 105a, 105b mounted to the distal end of shaft 100. Electrodes 105a, 105b are electrically connected to power supply as described above and preferably have tips 107a, 107b with a screwdriver shape. The screwdriver shape provides a greater amount of "edges" to electrodes 105a, 105b, to increase the electric field intensity and current density at the edges and thereby improve the cutting ability as well as the ability to limit bleeding from the incised tissue (i.e., hemostasis).

Figure 11A:
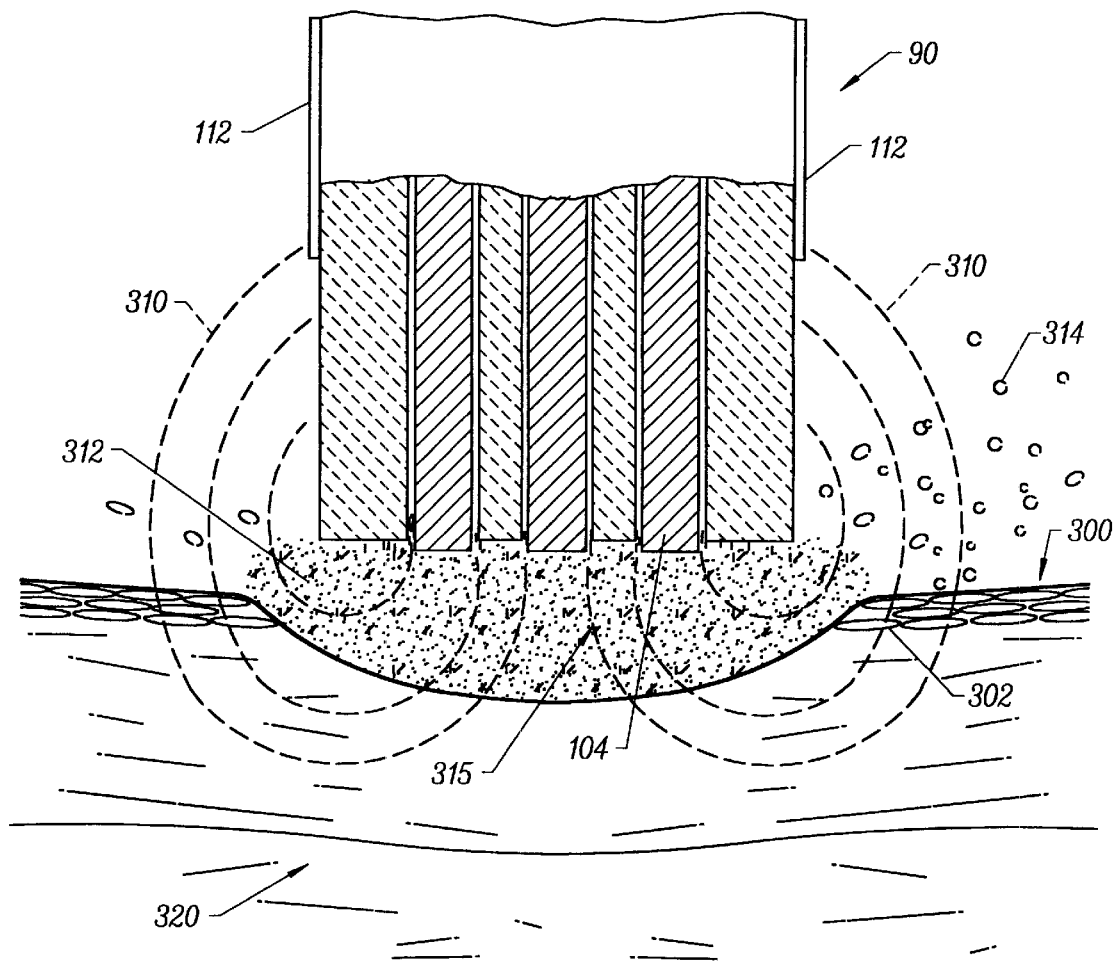
FIGS. 11A and 11B illustrate a detailed view of the ablation of tissue according to the present invention.
Figure 11B:
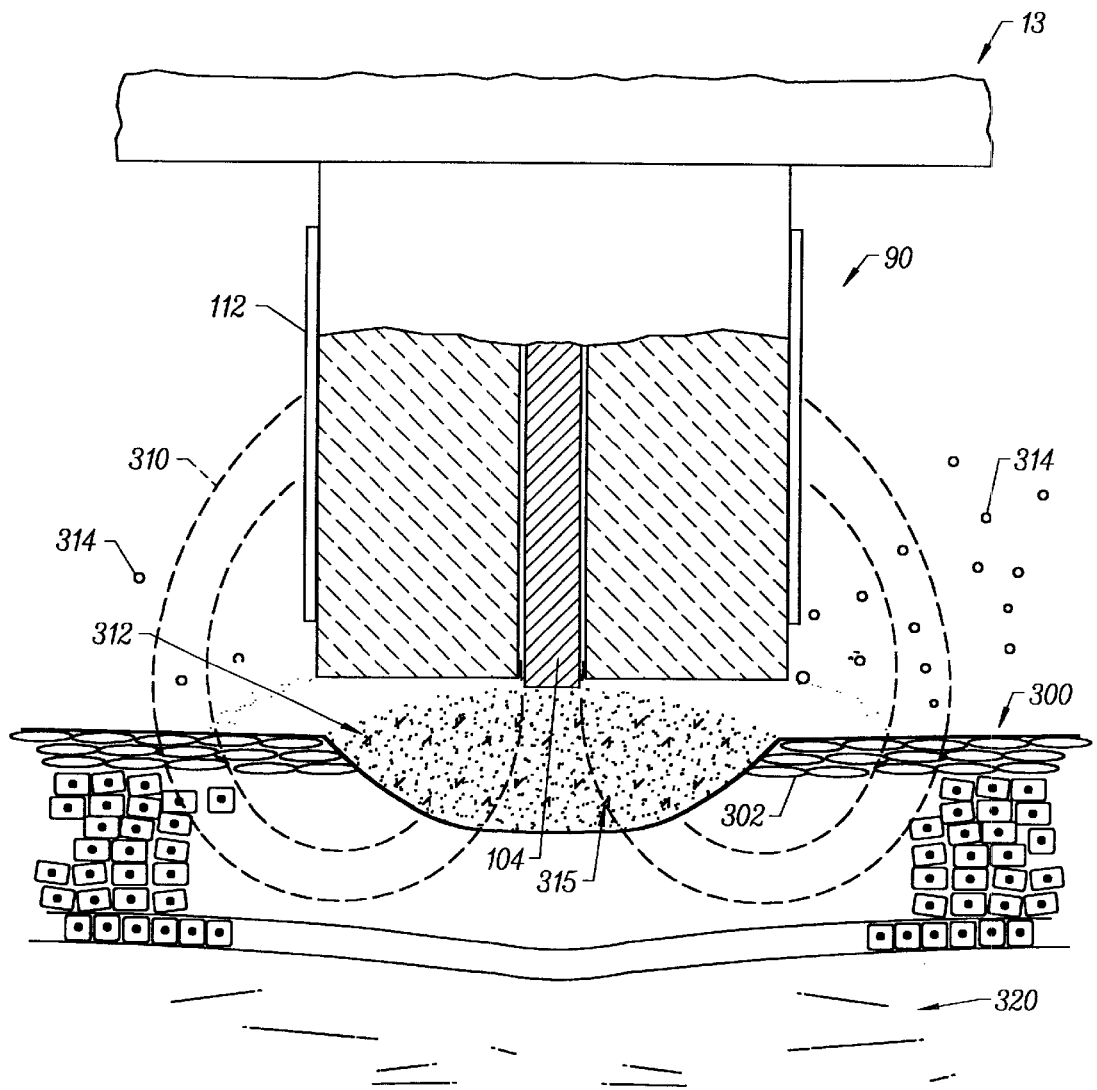

FIGS. 11A and 11B illustrate the present invention in the ablation mode. As shown, the high frequency voltage difference applied between the active electrodes 104 (single active electrode 104 in FIG. 11B) and the return electrode 112 is sufficient to convert the electrically conductive fluid (not shown) between the target tissue 302 and electrode terminal(s)104 into an ionized vapor layer 312 or plasma. As a result of the applied voltage difference between electrode terminal(s) 104 and the target tissue 3Q2 (i.e., the voltage gradient across the plasma layer 312), charged particles 315 in the plasma (viz., electrons) are accelerated towards the tissue. At sufficiently high voltage differences, these charged particles 315 gain sufficient energy to cause dissociation of the molecular bonds within tissue structures. This molecular dissociation is accompanied by the volumetric removal (i.e., ablative sublimation) of tissue and the production of low molecular weight gases 314, such as oxygen, nitrogen, carbon dioxide, hydrogen and methane. The short range of the accelerated charged particles 315 within the tissue confines the molecular dissociation process to the surface layer to minimize damage and necrosis to the underlying tissue 320.

In some embodiments, the gases 314 will be aspirated through opening 209 and suction tube 211 (see FIGS. 2 and 3) to a vacuum source. In addition, excess electrically conductive fluid, and other fluids (e.g., blood) will be aspirated from the target site 300 to facilitate the surgeon's view. During ablation of the tissue, the residual heat generated by the current flux lines (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure. Once the blockage has been removed, aeration and drainage are reestablished to allow the sinuses to heal and return to their normal function.

Figure 12B:
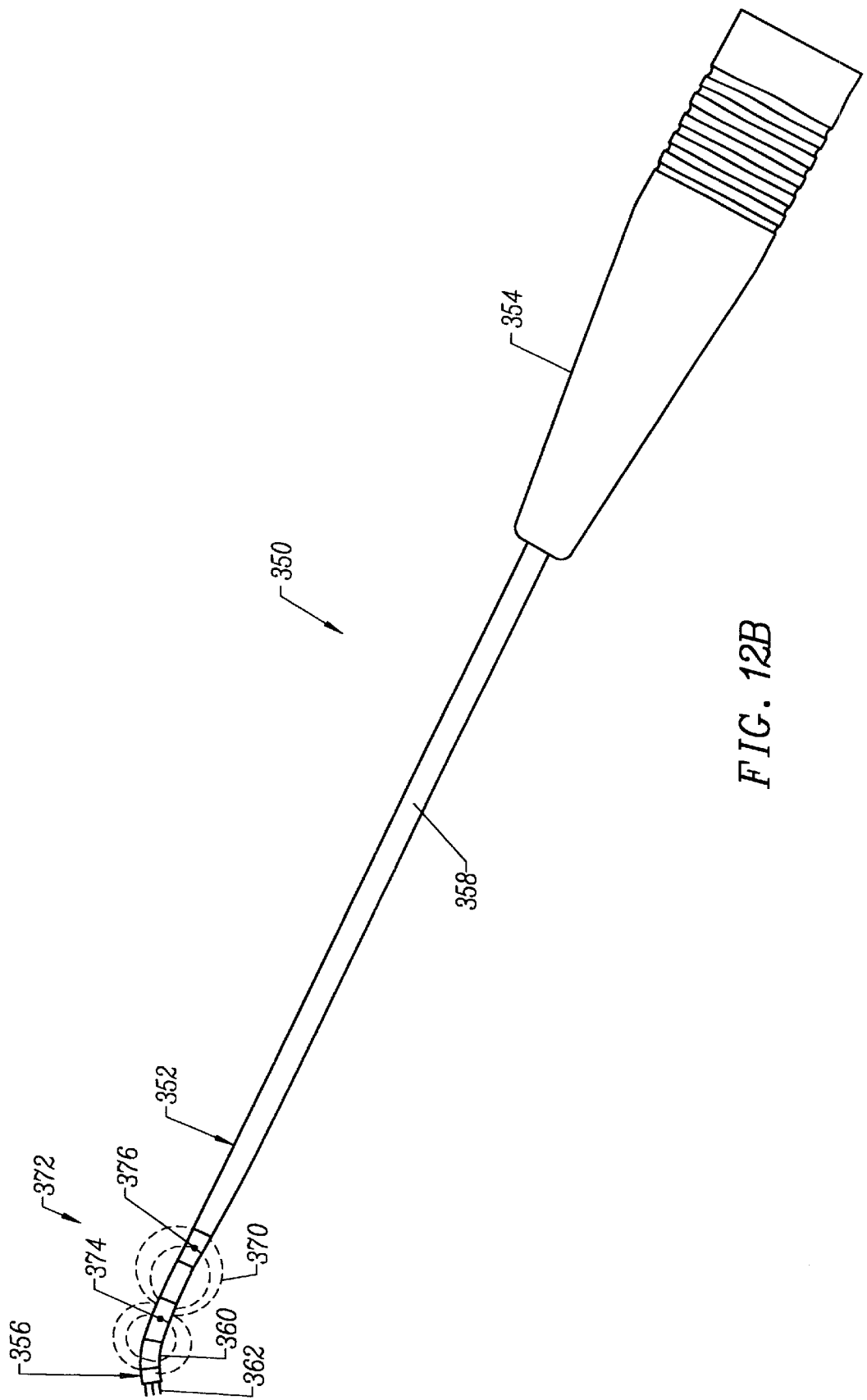

FIGS. 12A–12D and 13 illustrate embodiments of an electrosurgical probe 350 specifically designed for the treatment of obstructive sleep disorders, such as sleep apnea or snoring. Referring to FIG. 12A, probe 350 comprises an electrically conductive shaft 352, a handle 354 coupled to the proximal end of shaft 352 and an electrically insulating support member 356 at the distal end of shaft 352. Probe 350 further includes a shrink wrapped insulating sleeve 358 over shaft 352, and exposed portion of shaft 352 that functions as the return electrode 360. In the representative embodiment, probe 350 comprises a plurality of active electrodes 362 extending from the distal end of support member 356. As shown, return electrode 360 is spaced a further distance from active electrodes 362 than in the embodiments described above. In this embodiment, the return electrode 360 is spaced a distance of about 2.0 to 50 mm, preferably about 5 to 25 mm. In addition, return electrode 360 has a larger exposed surface area than in previous embodiments, having a length in the range of about 2.0 to 40 mm, preferably about 5 to 20 mm. Accordingly, electric current passing from active electrodes 362 to return electrode 360 will follow a current flow path 370 that is further away from shaft 352 than in the previous embodiments. In some applications, this current flow path 370 results in a deeper current penetration into the surrounding tissue with the same voltage level, and thus increased thermal heating of the tissue. As discussed above, this increased thermal heating may have advantages in some applications of treating obstructive sleep disorders. Typically, it is desired to achieve a tissue temperature in the range of about 60° C. to 100° C. to a depth of about 0.2 to 5 mm, usually about 1 to 2 mm. The voltage required for this thermal damage will partly depend on the electrode configurations, the conductivity of the tissue and the area immediately surrounding the electrodes, the time period in which the voltage is applied and the depth of tissue damage desired. With the electrode configurations described in FIGS. 12–14, the voltage level for thermal heating will usually be in the range of about 20 to 300 volts rms, preferably about 60 to 200 volts rms. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required. If the voltage is too high, however, the surface tissue may be vaporized, debulked or ablated, which is undesirable.

In alternative embodiments, the electrosurgical system used in conjunction with probe 350 may include a dispersive return electrode 450 (see FIG. 14) for switching between bipolar and monopolar modes. In this embodiment, the system will switch between an ablation mode, where the dispersive pad 450 is deactivated and voltage is applied between active and return electrodes 362, 360, and a subablation or thermal heating mode, where the active electrode (s) 362 and deactivated and voltage is applied between the dispersive pad 450 and the return electrode 360. In the subablation mode, a lower voltage is typically applied and the return electrode 360 functions as the active electrode to provide thermal heating and/or coagulation of tissue surrounding return electrode 360.

FIG. 12B illustrates yet another embodiment of the present invention. As shown, electrosurgical probe 350 comprises an electrode assembly 372 having one or more active electrode(s) 362 and a proximally spaced return electrode 360 as in previous embodiments. Return electrode 360 is typically spaced about 0.5 to 25 mm, preferably 1.0 to 5.0 mm from the active electrode(s) 362, and has an exposed length of about 1 to 20 mm. In addition, electrode assembly 372 includes two additional electrodes 374, 376 spaced axially on either side of return electrode 360. Electrodes 374, 376 are typically spaced about 0.5 to 25 mm, preferably about 1 to 5 mm from return electrode 360. In the representative embodiment, the additional electrodes 374, 376 are exposed portions of shaft 352, and the return electrode 360 is electrically insulated from shaft 352 such that a voltage difference may be applied between electrodes 374, 376 and electrode 360. In this embodiment, probe 350 may be used in at least two different modes, an ablation mode and a subablation or thermal heating mode. In the ablation mode, voltage is applied between active electrode (s) 362 and return electrode 360 in the presence of electrically conductive fluid, as described above. In the ablation mode, electrodes 374, 376 are deactivated. In the thermal heating or coagulation mode, active electrode(s) 362 are deactivated and a voltage difference is applied between electrodes 374, 376 and electrode 360 such that a high frequency current 370 flows therebetween, as shown in FIG. 12B. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 372, 374.

Figure 12C:
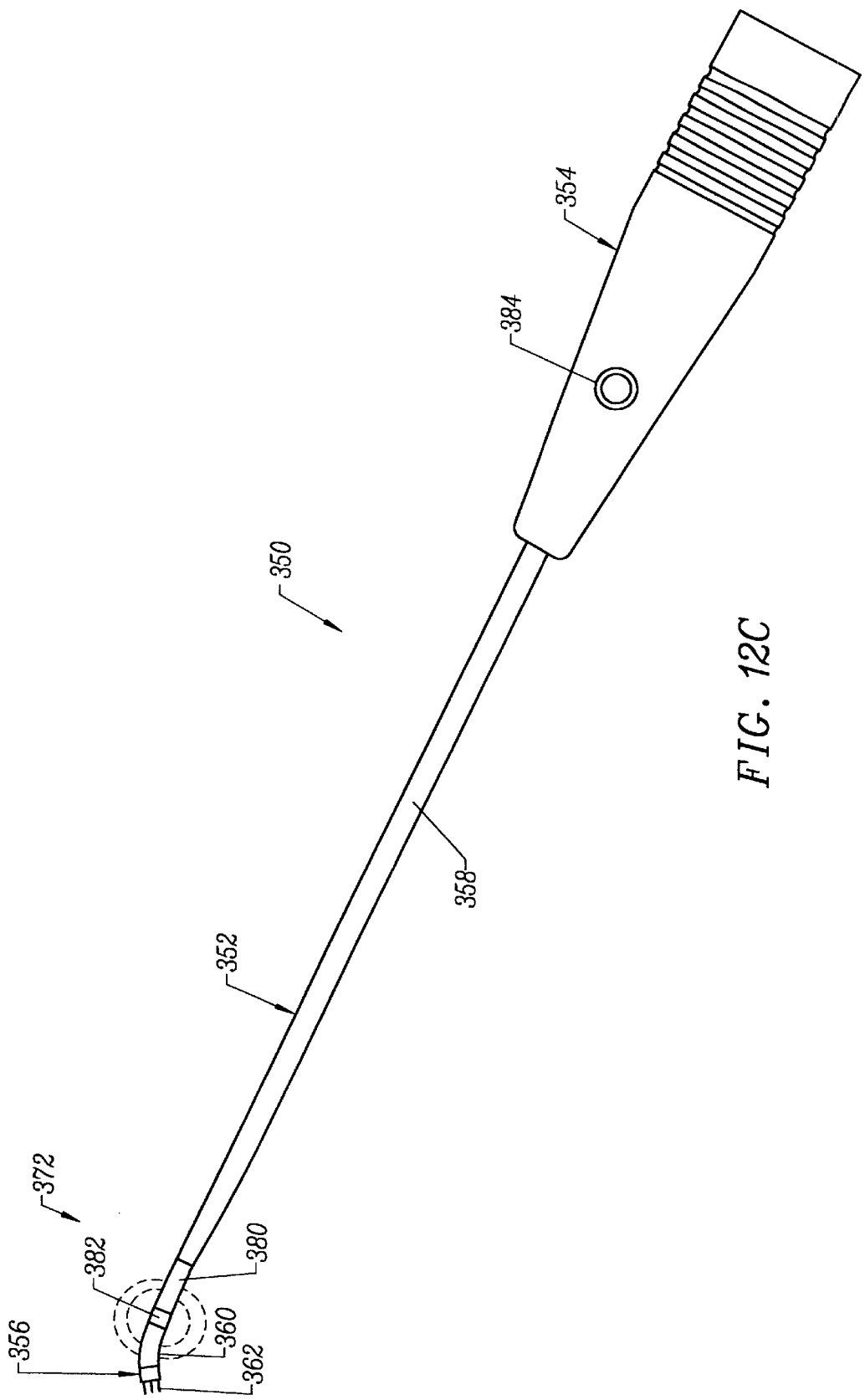

FIG. 12C illustrates another embodiment of probe 350 incorporating an electrode assembly 372 having one or more active electrode(s) 362 and a proximally spaced return electrode 360 as in previous embodiments. Return electrode 360 is typically spaced about 0.5 to 25 mm, preferably 1.0 to 5.0 mm from the active electrode(s) 362, and has an exposed length of about 1 to 20 mm. In addition, electrode assembly 372 includes a second active electrode 380 separated from return electrode 360 by an electrically insulating spacer 382. In this embodiment, handle 354 includes a switch 384 for toggling probe 350 between at least two different modes, an ablation mode and a subablation or thermal heating mode. In the ablation mode, voltage is applied between active electrode(s) 362 and return electrode 360 in the presence of electrically conductive fluid, as described above. In the ablation mode, electrode 380 deactivated. In the thermal heating or coagulation mode, active electrode(s) 362 may be deactivated and a voltage difference is applied between electrode 380 and electrode 360 such that a high frequency current 370 flows therebetween. Alternatively, active electrode(s) 362 may not be deactivated as the higher resistance of the smaller electrodes may automatically send the electric current to electrode 380 without having to physically decouple electrode(s) 362 from the circuit. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 380.

Of course, it will be recognized that a variety of other embodiments may be used to accomplish similar functions as the embodiments described above. For example, electrosurgical probe 350 may include a plurality of helical bands formed around shaft 352, with one or more of the helical bands having an electrode coupled to the portion of the band such that one or more electrodes are formed on shaft 352 spaced axially from each other.

Figure 12D:
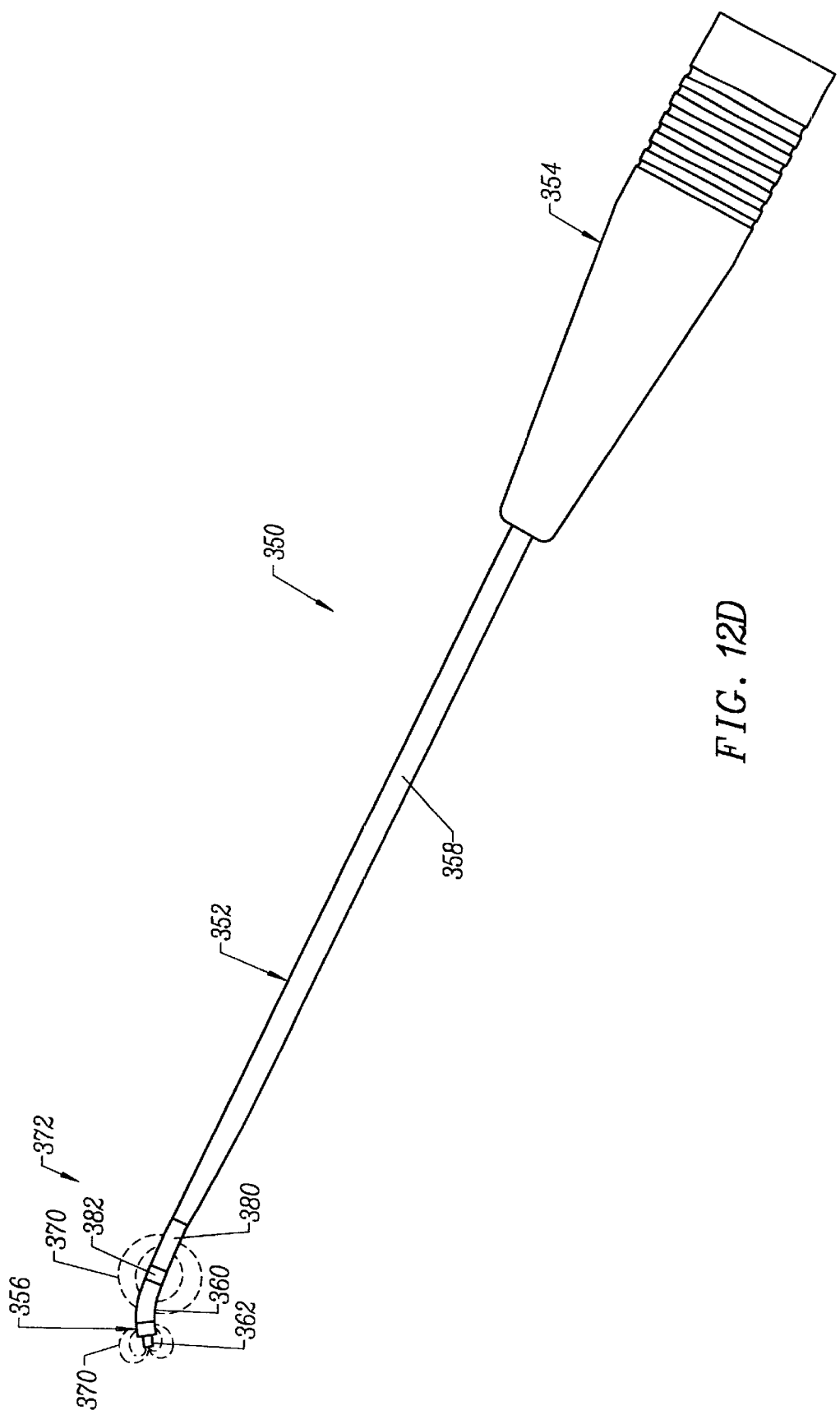

FIG. 12D illustrates another embodiment of the invention designed for channeling through tissue and creating lesions therein to treat turbinates and/or snoring and sleep apnea. As shown, probe 350 is similar to the probe in FIG. 12C having a return electrode 360 and a third, coagulation electrode 380 spaced proximally from the return electrode 360. In this embodiment, active electrode 362 comprises a single electrode wire extending distally from insulating support member 356. Of course, the active electrode 362 may have a variety of configurations to increase the current densities on its surfaces, e.g., a conical shape tapering to a distal point, a hollow cylinder, loop electrode and the like. In the representative embodiment, support members 356 and 382 are constructed of inorganic material, such as ceramic, glass, silicone and the like. The proximal support member 382 may also comprise a more conventional organic material as this support member 382 will generally not be in the presence of a plasma that would otherwise etch or wear away an organic material.

The probe 350 in FIG. 12D does not include a switching element. In this embodiment, all three electrodes are activated when the power supply is activated. The return electrode 360 has an opposite polarity from the active and coagulation electrodes 362, 380 such that current 370 flows from the latter electrodes to the return electrode 360 as shown. In the preferred embodiment, the electrosurgical system includes a voltage reduction element or a voltage reduction circuit for reducing the voltage applied between the coagulation electrode 380 and return electrode 360. The voltage reduction element functions as a voltage drop between the power supply and the coagulation electrode 380 to, in effect, allow the power supply 28 to apply two different voltages simultaneously to two different electrodes. Thus, for channeling through tissue, the operator may apply a voltage sufficient to provide ablation of the tissue at the tip of the probe (i.e., tissue adjacent to the active electrode 362). At the same time, the voltage applied to the coagulation electrode 380 will be insufficient to ablate tissue. For thermal heating or coagulation of tissue, for example, the voltage reduction element will serve to reduce a voltage of about 100 to 300 volts rms to about 45 to 90 volts rms, which is a suitable voltage for coagulation of tissue without ablation (e.g., molecular dissociation) of the tissue.

In the representative embodiment, the voltage reduction element is a capacitor (not shown) coupled to the power supply and coagulation electrode 380. The capacitor usually has a capacitance of about 100 to 1500 pF (at 500 volts) and preferably about 200 to 1000 pF (at 500 volts). In the representative embodiment, the voltage reduction element comprises two capacitors connected in series with the coagulation electrode 380 or shaft 358. The capacitors each have a capacitance of about 350–450 pF to form a single capacitance of about 700–900 pF. Of course, the capacitor may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 350 may include a coded resistor (not shown) that is constructed to lower the voltage applied between the return and coagulation electrodes 360, 380. In addition, electrical circuits may be employed for this purpose.

Of course, for some procedures, the probe will typically not require a voltage reduction element. Alternatively, the probe may include a voltage increasing element or circuit, if desired. Alternatively or additionally, the cable 22 that couples the power supply 28 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor. Further, it should be noted that the present invention can be used with a power supply that is adapted to apply two different voltages within the selected range for treatment of tissue. In this embodiment, a voltage reduction element or circuitry may not be desired.

In one specific embodiment, the probe 350 is manufactured by first inserting an electrode wire (active electrode 362) through a ceramic tube (insulating member 360) such that a distal portion of the wire extends through the distal portion of the tube, and bonding the wire to the tube, typically with an appropriate epoxy. A stainless steel tube (return electrode 356) is then placed over the proximal portion of the ceramic tube, and a wire (e.g., nickel wire) is bonded, typically by spot welding, to the inside surface of the stainless steel tube. The stainless steel tube is coupled to the ceramic tube by epoxy, and the device is cured in an oven or other suitable heat source. A second ceramic tube (insulating member 382) is then placed inside of the proximal portion of the stainless steel tube, and bonded in a similar manner. The shaft 358 is then bonded to the proximal portion of the second ceramic tube, and an insulating sleeve (e.g. polyimide) is wrapped around shaft 358 such that only a distal portion of the shaft is exposed (i.e., coagulation electrode 380). The nickel wire connection will extend through the center of shaft 358 to connect return electrode 356 to the power supply. The active electrode 362 may form a distal portion of shaft 358, or it may also have a connector extending through shaft 358 to the power supply.

In use, the physician positions active electrode 362 adjacent to the tissue surface to be treated (i.e., the soft palate, uvula, tongue, turbinates or uvula). The power supply is activated to provide an ablation voltage between active and return electrodes 362, 360 and a coagulation or thermal heating voltage between coagulation and return electrodes 360, 380. An electrically conductive fluid is then provided around active electrode 362, and in the junction between the active and return electrodes 360, 362 to provide a current flow path therebetween. This may be accomplished in a variety of manners, as discussed above. The active electrode 362 is then advanced through the space left by the ablated tissue to form a channel. During ablation, the electric current between the coagulation and return electrode is typically insufficient to cause any damage to the surface of the tissue as these electrodes pass through the tissue surface into the channel created by active electrode 362. Once the physician has formed the channel to the appropriate depth, he or she will cease advancement of the active electrode, and will either hold the instrument in place for 1 to 10 seconds, or will immediately remove the distal tip of the instrument from the channel (see detailed discussion of this below). In either event, when the active electrode is no longer advancing, it will eventually stop ablating tissue.

Prior to entering the channel formed by the active electrode 362, an open circuit exists between return and coagulation electrodes 360, 380. Once coagulation electrode 380 enters this channel, electric current will flow from coagulation electrode 380, through the tissue surrounding the channel, to return electrode 360. This electric current will heat the tissue immediately surrounding the channel to coagulate any severed vessels at the surface of the channel. If the physician desires, the instrument may be held within the channel for a period of time to create a lesion around the channel, as discussed in more detail below.

In alternative embodiments, the distal portion of shaft 352 of probe 350 may have different angles relative to the proximal handle 354. For example, for treating turbinates, applicant has found that the distal portion of shaft 352 may have extend at an angle of about 35° to 55° relative to the proximal portion of shaft or handle 354. For treating snoring or sleep apnea in the soft palate or tongue, the distal portion of shaft 352 may extend at an angle of about 50° to 70° relative to the proximal portion of the shaft.

Figure 13:
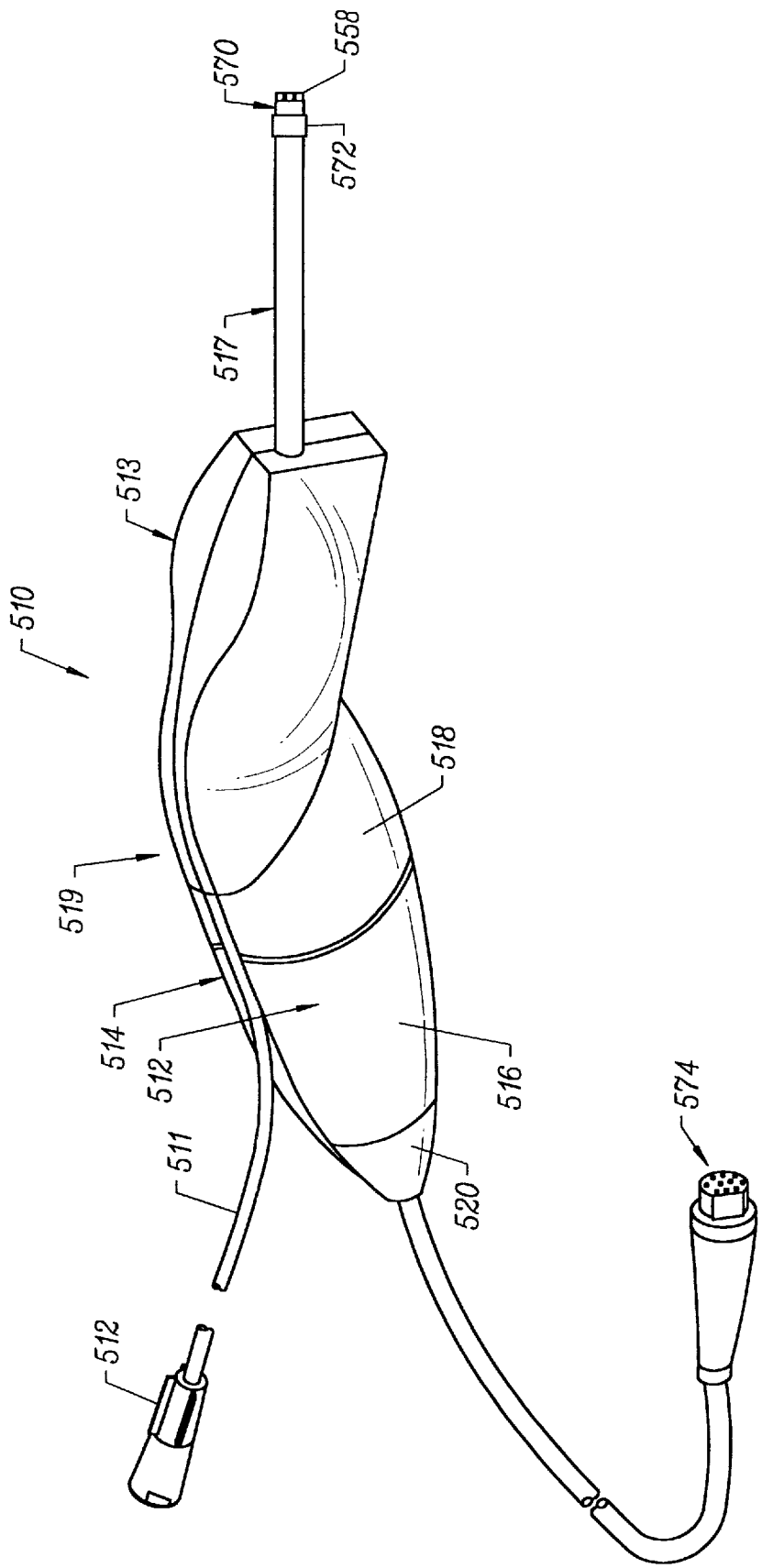
FIG. 13 illustrates an alternative embodiment of an electrosurgical probe for treating obstructive sleep disorders.

FIG. 13 illustrates yet another embodiment of the present invention for forming small channels or holes in tissue, as described in more detail below. In this embodiment, an exemplary electrosurgical probe 510 comprises a handle 519, which preferably comprises a disposable distal portion 513 removably coupled to a proximal reusable portion 512, and an elongate shaft 517 extending from distal portion 513 of handle 519. Shaft 517 is also disposable, and preferably removably coupled to distal portion 513 of the handle. The proximal and distal portions of handle 512 typically comprise a plastic material that is easily molded into a suitable shape for handling by the surgeon. Handle 519 defines an inner cavity (not shown) that houses the electrical connections 574, and provides a suitable interface for connection to an electrical connecting cable (not shown). In the exemplary embodiment, the proximal portion of handle 519 is constructed so that it can be re-used by sterilizing handle 519 between surgical procedures. However, it should be understood that both the proximal and distal portions of handle 519 may be reusable, or both of these handle portions may be disposable, if desired.

Shaft 517 is preferably sized to provide access to the patient's mouth and throat, typically through the patient's mouth. Accordingly, shaft 517 preferably has a length in the range of about 4 to 25 cm and a diameter less than 1 cm. For treating obstructive sleep disorders, the shaft 517 will also preferably be sized for forming small holes or channels in the tongue, palate, tonsils and/or uvula and, therefore, will have a diameter less than 3 mm, preferably less than about 1 mm. Alternatively, shaft 517 may have a distal portion that is smaller than the rest of shaft for forming such holes. As shown in FIG. 13, shaft 517 includes an electrically insulating electrode support member 570 extending from the distal end of shaft 517 (usually about 0.5 to 20 mm) to provide support for a plurality of electrically isolated electrode terminals 558. Alternatively, electrode support member 570 may be recessed from the distal end of shaft 517 to help confine the electrically conductive fluid around the electrode terminals 558 during the surgical procedure, as discussed above.

In the embodiment shown in FIG. 13, probe 510 includes an annular return electrode 572 for completing the current path between electrode terminals 558 and a high frequency power supply 28. Return electrode 572 is spaced proximally from electrode terminal(s) 558 a sufficient distance to avoid arcing therebetween. In addition, return electrode 572 is positioned such that, when electrode terminal(s) 558 are brought adjacent a tissue structure, return electrode 572 is spaced away from the tissue structure so that the tissue structure cannot, at least by itself, complete the current flow path between electrode terminal(s) 558 and return electrode 572.

To complete the current path between electrode terminals 558 and return electrode 572, electrically conducting fluid (e.g., isotonic saline or electrically conducting gel) is located between the active and return electrodes during a surgical procedure. In the representative embodiment, probe 510 includes a fluid tube 511 for delivering electrically conductive fluid to the target site. Fluid tube 511 is sized to extend through a groove 514 in handle 511 and through an inner cavity (not shown) in shaft 517 to a distal opening (not shown) located adjacent electrode support member 570. Tube 510 preferably extends all the way through the inner cavity to the distal opening to eliminate any possible fluid ingress into the cavity. As shown in FIG. 13, fluid tube 510 includes a proximal connector 512 for coupling to an electrically conductive fluid source (not shown). Probe 510 will also include a valve or equivalent structure for controlling the flow rate of the electrically conducting fluid to the target site. In the representative embodiment, handle 19 comprises a main body 518, 520 and a rotatable sleeve 516 for controlling fluid flow through tube 510. Rotation of sleeve 516 crimps tube 510 to limit or complete shut off flow therethrough. Of course, this fluid control may be provided by a variety of other input and valve devices, such as switches, buttons, etc.

Figure 14:
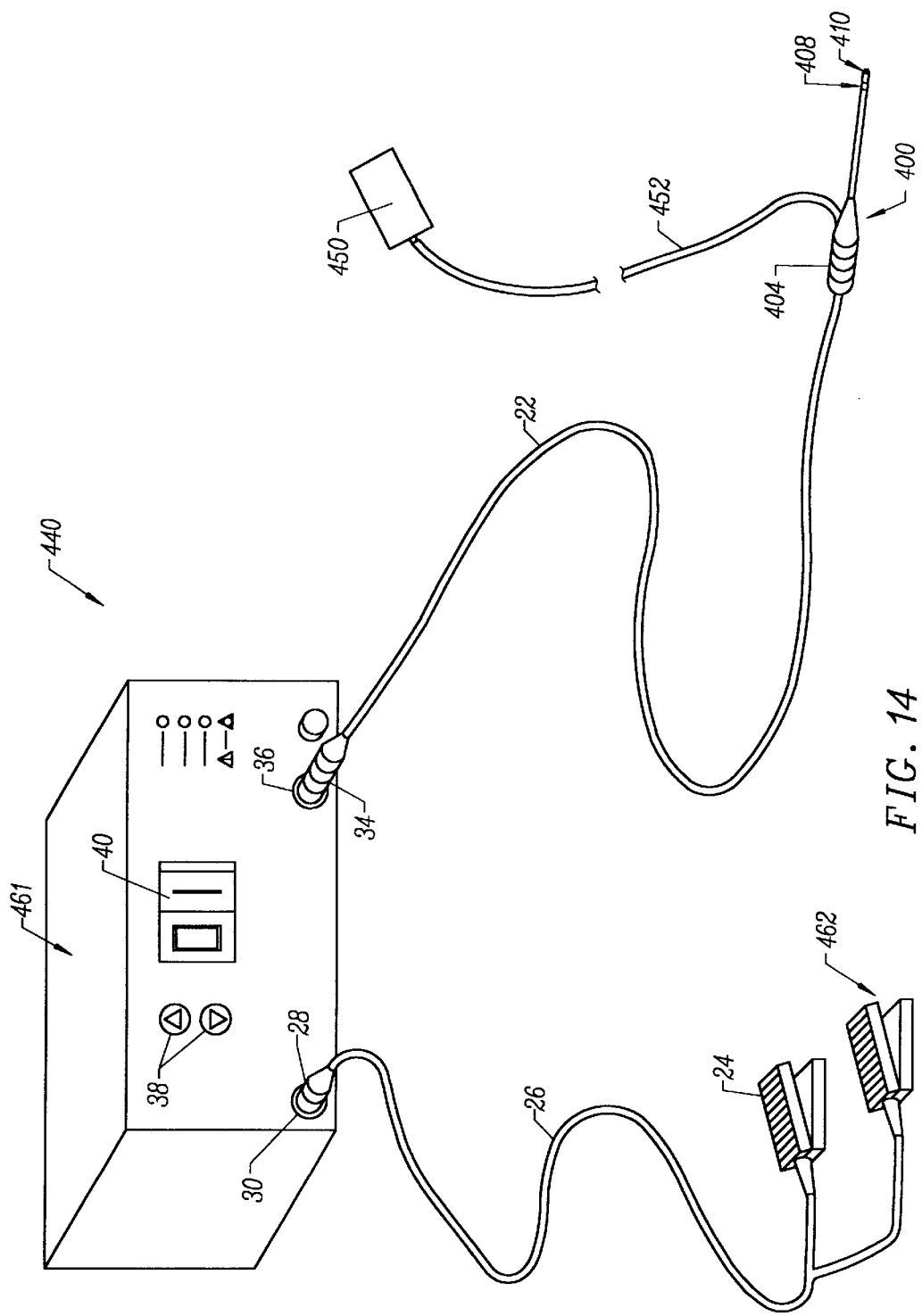
FIG. 14 illustrates an electrosurgical system incorporating a dispersive return pad for monopolar and/or bipolar operations.

FIG. 14 illustrates yet another embodiment of an electrosurgical system 440 incorporating a dispersive return pad 450 attached to the electrosurgical probe 400. In this embodiment, the invention functions in the bipolar mode as described above. In addition, the system 440 may function in a monopolar mode in which a high frequency voltage difference is applied between the active electrode(s) 410, and the dispersive return pad 450. In the exemplary embodiment, the pad 450 and the probe 400 are coupled together, and are both disposable, single-use items. The pad 450 includes an electrical connector 452 that extends into handle 404 of probe 400 for direct connection to the power supply. Of course, the invention would also be operable with a standard return pad that connects directly to the power supply. In this embodiment, the power supply 461 will include a switch, e.g., a foot pedal 462, for switching between the monopolar and bipolar modes. In the bipolar mode, the return path on the power supply is coupled to return electrode 408 on probe 400, as described above. In the monopolar mode, the return path on the power supply is coupled to connector 452 of pad 450, active electrode(s) 410 are decoupled from the electrical circuit, and return electrode 408 functions as the active electrode. This allows the surgeon to switch between bipolar and monopolar modes during, or prior to, the surgical procedure (discussed in more detail below in conjunction with FIGS. 18–21). In some cases, it may be desirable to operate in the monopolar mode to provide deeper current penetration and, thus, a greater thermal heating of the tissue surrounding the return electrodes. In other cases, such as ablation of tissue, the bipolar modality may be preferable to limit the current penetration to the tissue.

In one configuration, the dispersive return pad 450 is adapted for coupling to an external surface of the patient in a region substantially close to the target region. For example, during the treatment of tissue in the head and neck, the dispersive return pad is designed and constructed for placement in or around the patient's shoulder, upper back or upper chest region. This design limits the current path through the patient's body to the head and neck area, which minimizes the damage that may be generated by unwanted current paths in the patient's body, particularly by limiting current flow through the patient's heart. The return pad is also designed to minimize the current densities at the pad, to thereby minimize patient skin burns in the region where the pad is attached.

Figure 15:
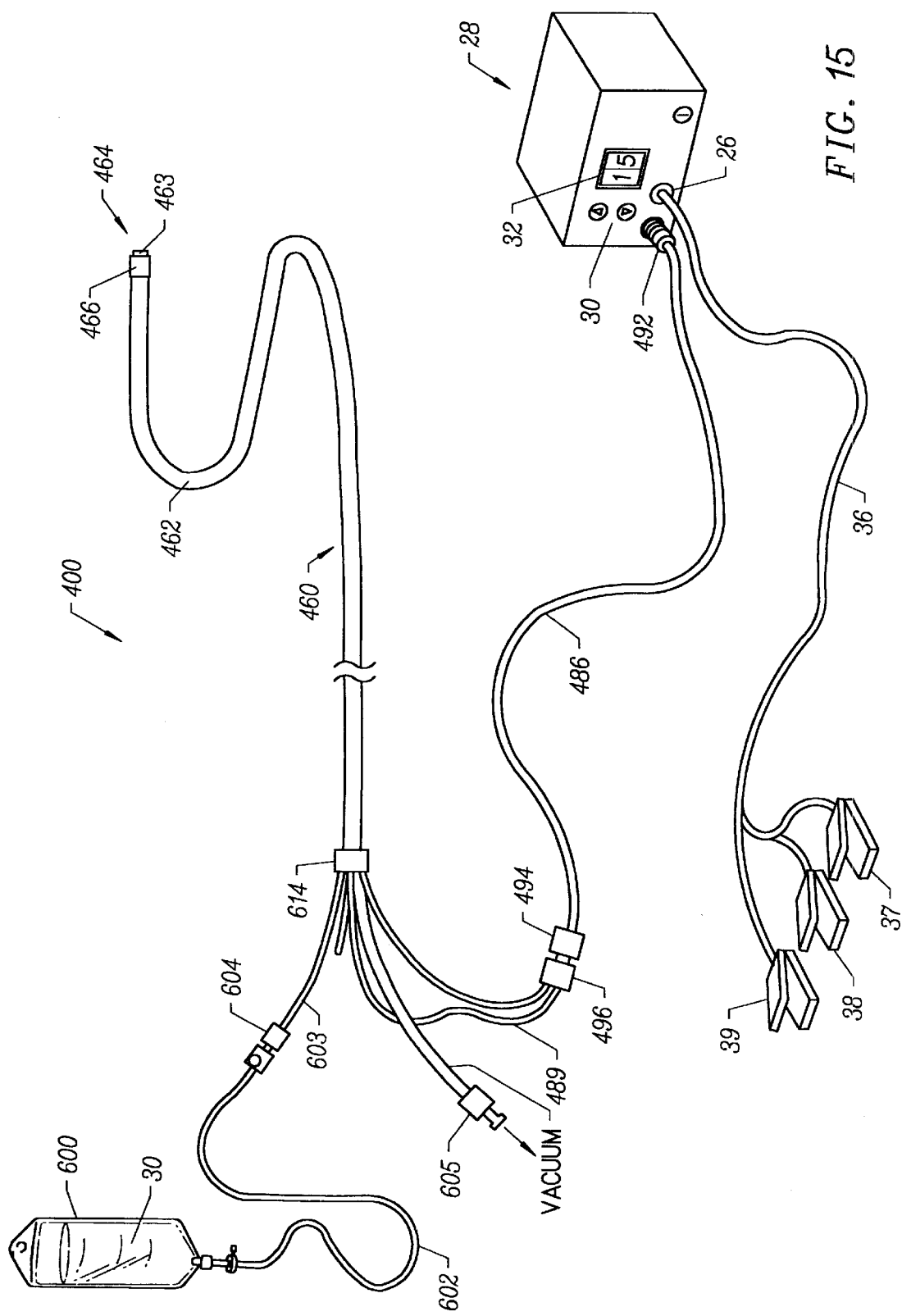
FIG. 15 illustrates a catheter system for electrosurgical treatment of body structures within the head and neck according to the present invention.
Figure 16:
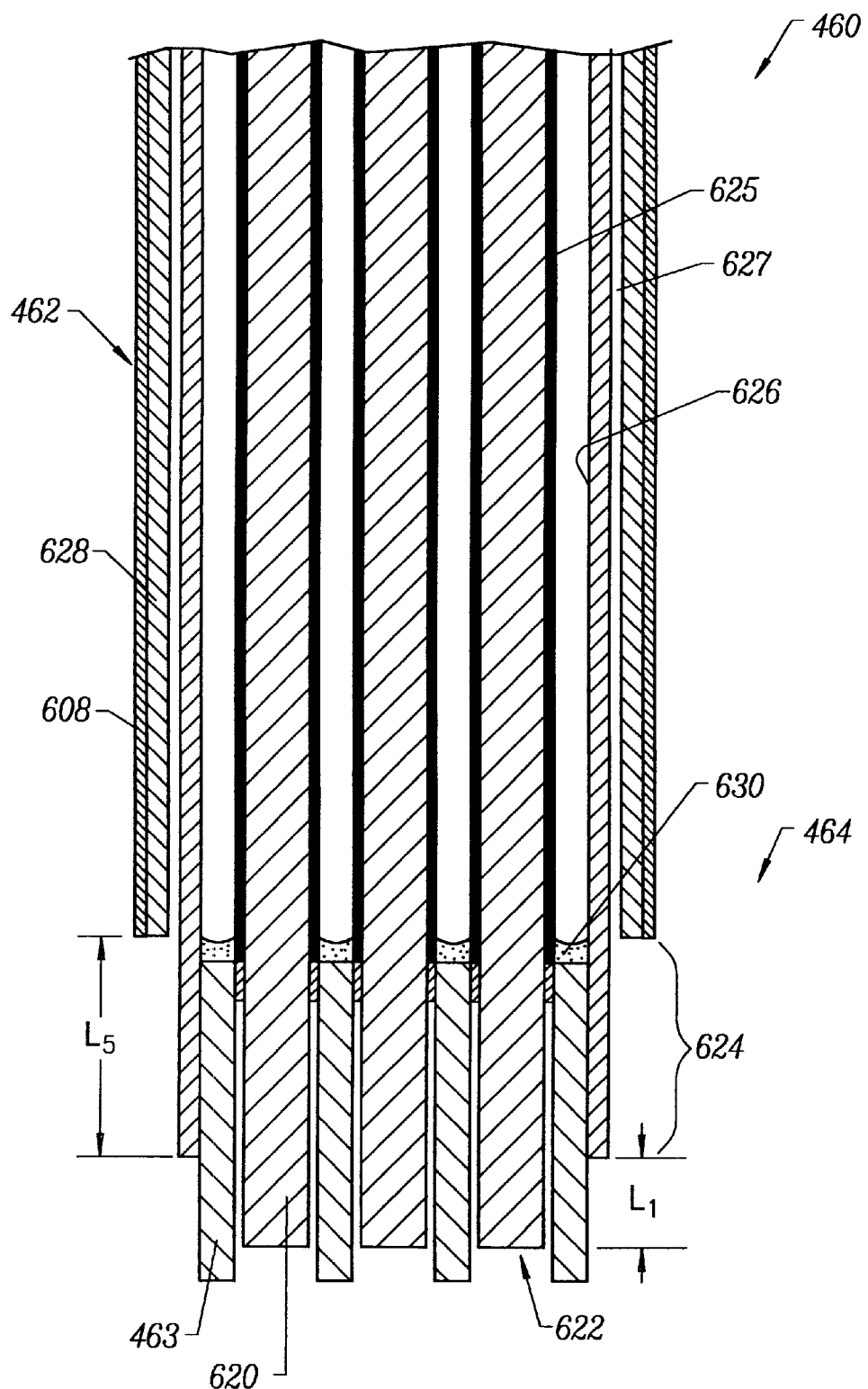
FIG. 16 is a cross-section view of a working end of a catheter according to one embodiment of the present invention.

Referring to FIGS. 15–17, the electrosurgical device according to the present invention may also be configured as a catheter system 400. As shown in FIG. 15, a catheter system 400 generally comprises an electrosurgical catheter 460 connected to a power supply 28 by an interconnecting cable 486 for providing high frequency voltage to a target tissue and an irrigant reservoir or source 600 for providing electrically conducting fluid to the target site. Catheter 460 generally comprises an elongate, flexible shaft body 462 including a tissue removing or ablating region 464 at the distal end of body 462. The proximal portion of catheter 460 includes a multi-lumen fitment 614 which provides for interconnections between lumens and electrical leads within catheter 460 and conduits and cables proximal to fitment 614. By way of example, a catheter electrical connector 496 is removably connected to a distal cable connector 494 which, in turn, is removably connectable to generator 28 through connector 492. One or more electrically conducting lead wires (not shown) within catheter 460 extend between one or more active electrodes 463 at tissue ablating region 464 and one or more corresponding electrical terminals (also not shown) in catheter connector 496 via active electrode cable branch 487. Similarly, one or more return electrodes 466 at tissue ablating region 464 are coupled to a return electrode cable branch 489 of catheter connector 496 by lead wires (not shown). Of course, a single cable branch (not shown) may be used for both active and return electrodes.

Catheter body 462 may include reinforcing fibers or braids (not shown) in the walls of at least the distal ablation region 464 of body 462 to provide responsive torque control for rotation of electrode terminals during tissue engagement. This rigid portion of the catheter body 462 preferably extends only about 7 to 10 mm while the remainder of the catheter body 462 is flexible to provide good trackability during advancement and positioning of the electrodes adjacent target tissue.

Conductive fluid 30 is provided to tissue ablation region 464 of catheter 460 via a lumen (not shown in FIG. 15) within catheter 460. Fluid is supplied to lumen from the source along a conductive fluid supply line 602 and a conduit 603, which is coupled to the inner catheter lumen at multi-lumen fitment 614. The source of conductive fluid (e.g., isotonic saline) may be an irrigant pump system (not shown) or a gravity-driven supply, such as an irrigant reservoir 600 positioned several feet above the level of the patient and tissue ablating region 8. A control valve 604 may be positioned at the interface of fluid supply line 602 and conduit 603 to allow manual control of the flow rate of electrically conductive fluid 30. Alternatively, a metering pump or flow regulator may be used to precisely control the flow rate of the conductive fluid.

System 400 further includes an aspiration or vacuum system (not shown) to aspirate liquids and gases from the target site. The aspiration system will usually comprise a source of vacuum coupled to fitment 614 by a aspiration connector 605.

FIGS. 16 and 17 illustrate the working end 464 of an electrosurgical catheter 460 constructed according to the principles of the present invention. As shown in FIG. 16, catheter 460 generally includes an elongated shaft 462 which may be flexible or rigid, and an electrode support member 620 coupled to the distal end of shaft 462. Electrode support member 620 extends from the distal end of shaft 462 (usually about 1 to 20 mm), and provides support for a plurality of electrically isolated electrode terminals 463. Electrode support member 620 and electrode terminals 463 are preferably secured to a tubular support member 626 within shaft 462 by adhesive 630.

The electrode terminals 463 may be constructed using round, square, rectangular or other shaped conductive metals. By way of example, the electrode terminal materials may be selected from the group including stainless steel, tungsten and its alloys, molybdenum and its alloys, titanium and its alloys, nickel-based alloys, as well as platinum and its alloys. Electrode support member 620 is preferably a ceramic, glass or glass/ceramic composition (e.g., aluminum oxide, titanium nitride). Alternatively, electrode support member 620 may include the use of high-temperature biocompatible plastics such as polyether-ether-keytone (PEEK) manufactured by Vitrex International Products, Inc. or polysulfone manufactured by GE Plastics. The adhesive 630 may, by way of example, be an epoxy (e.g., Master Bond EP42HT) or a silicone-based adhesive.

Figure 17A:
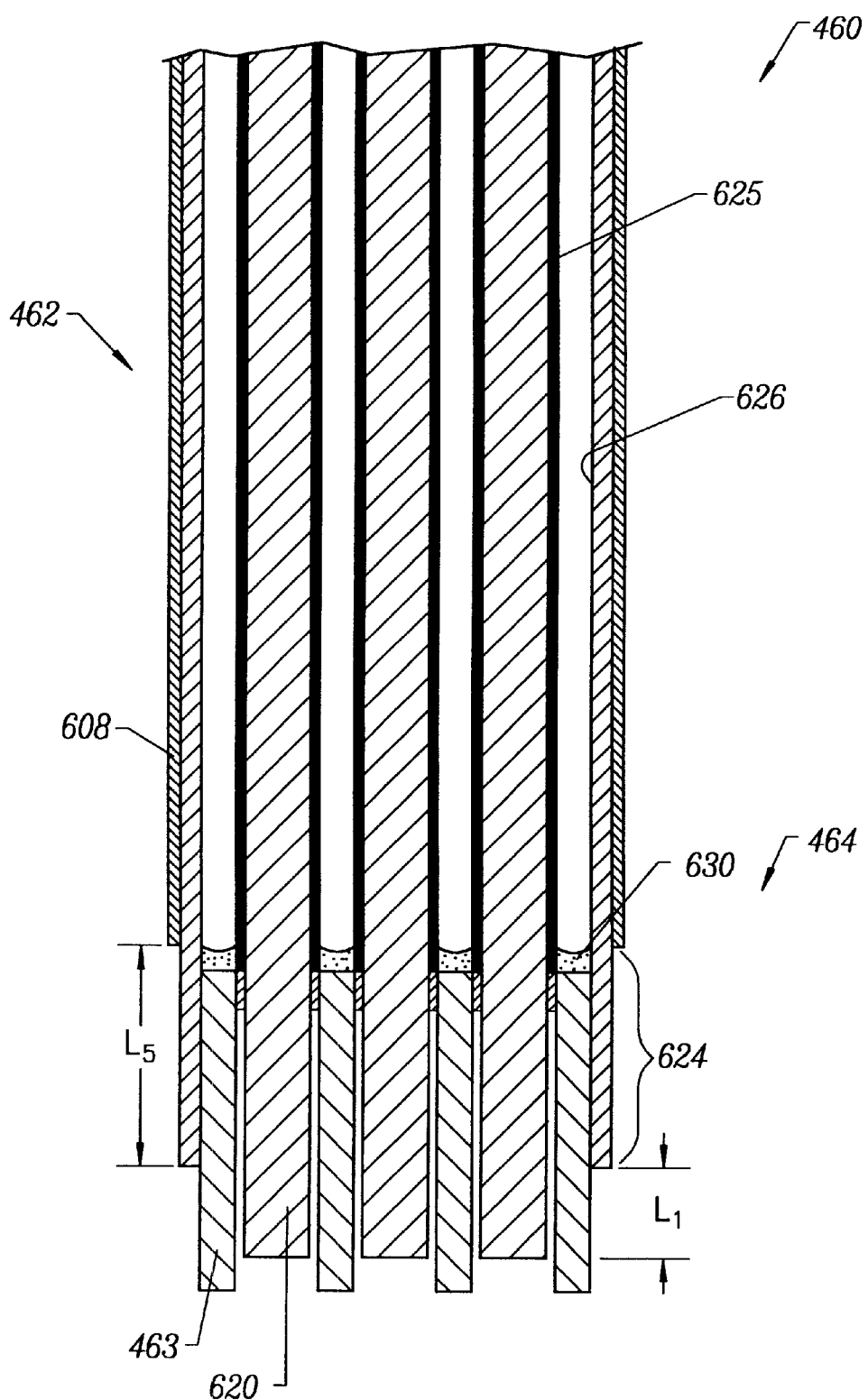
FIG. 17A is a cross-section view of a working end of a catheter according to a second embodiment of the present invention.
Figure 17B:
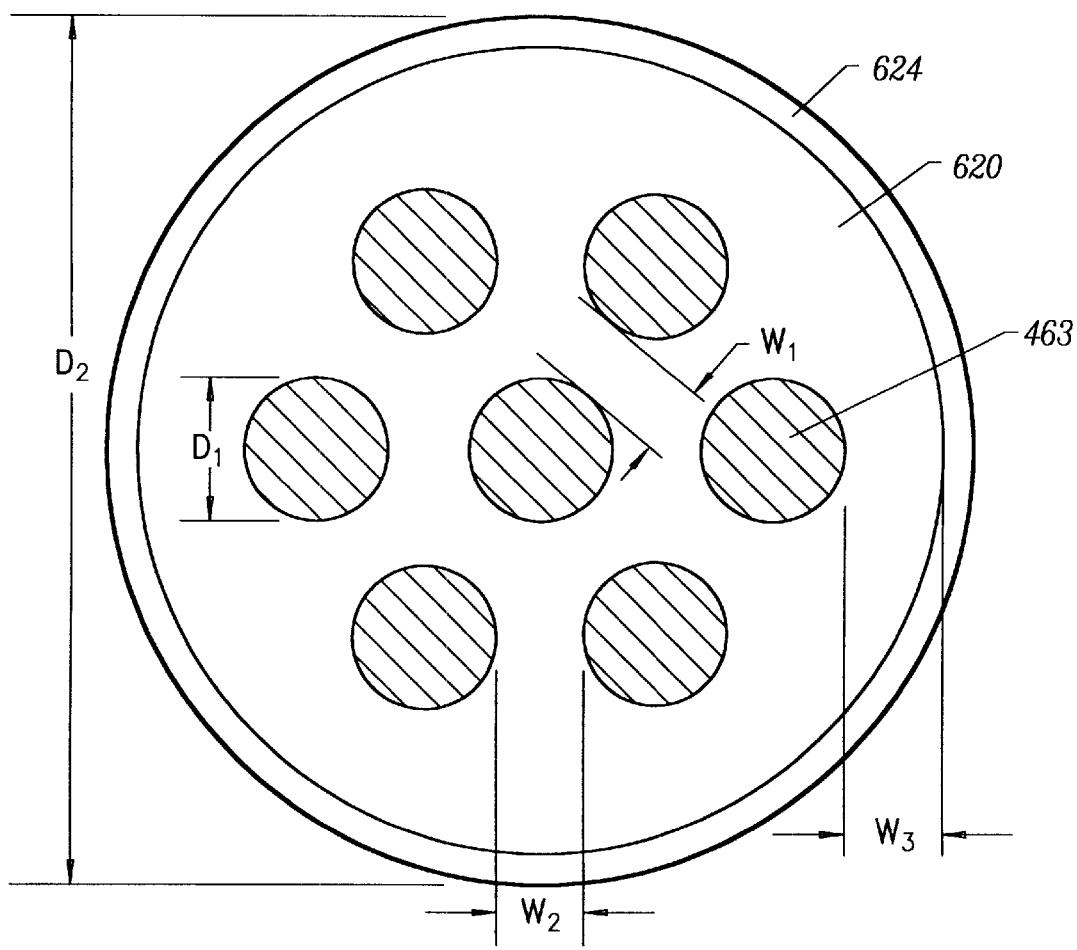
FIG. 17B is an end view of the catheter of FIG. 17A.

As shown in FIG. 17B, a total of 7 circular active electrodes or electrode terminals 463 are shown in a symmetrical pattern having an active electrode diameter, D1 in the range from 0.05 mm to 1.5 mm, more preferably in the range from 0.1 mm to 0.75 mm. The interelectrode spacings, W1 and W2 are preferably in the range from 0.1 mm to 1.5 mm and more preferably in the range from 0.2 mm to 0.75 mm. The distance between the outer perimeter of the electrode terminal 463 and the perimeter of the electrode support member, W3 is preferably in the range from 0.1 mm to 1.5 mm and more preferably in the range from 0.2 mm to 0.75 mm. The overall diameter, D2 of the working end 464 of catheter body 462 is preferably in the range from 0.5 mm to 10 mm and more preferably in the range from 0.5 mm to 5 mm. As discussed above, the shape of the active electrodes may be round, square, triangular, hexagonal, rectangular, tubular, flat strip and the like and may be arranged in a circularly symmetric pattern or may, by way of example, be arranged in a rectangular pattern, square pattern, or strip.

Catheter body 462 includes a tubular cannula 626 extending along body 462 radially outward from support member 620 and electrode terminals 463. The material for cannula 626 may be advantageously selected from a group of electrically conductive metals so that the cannula 626 functions as both a structural support member for the array of electrode terminals 463 as well as a return electrode 624. The support member 626 is connected to an electrical lead wire (not shown) at its proximal end within a connector housing (not shown) and continues via a suitable connector to power supply 28 to provide electrical continuity between one output pole of high frequency generator 28 and said return electrode 624. The cannula 626 may be selected from the group including stainless steel, copper-based alloys, titanium or its alloys, and nickel-based alloys. The thickness of the cannula 626 is preferably in the range from 0.08 mm to 1.0 mm and more preferably in the range from 0.1 mm to 0.4 mm.

As shown in FIG. 16, cannula 626 is covered with an electrically insulating sleeve 608 to protect the patient's body from the electric current. Electrically insulating sleeve 608 may be a coating (e.g., nylon) or heat shrinkable plastic (e.g., fluropolymer or polyester). The distal portion of the cannula 626 is left exposed to function as the return electrode 624. The length of the return electrode 624, L5 is preferably in the range from 1 mm to 30 mm and more preferably in the range from 2 mm to 20 mm. The spacing between the most distal portion of the return electrode 624 and the plane of the tissue treatment surface 622 of the electrode support member 620, L1 is preferably in the range from 0.5 mm to 30 mm and more preferably in the range from 1 mm to 20 mm. The thickness of the electrically insulating sleeve 608 is preferably in the range from 0.01 mm to 0.5 mm and more preferably in the range from 0.02 mm to 0.2 mm.

In the representative embodiment, the fluid path is formed in catheter by an inner lumen 627 or annular gap between the return electrode 624 and a second tubular support member 628 within shaft 462. This annular gap may be formed near the perimeter of the shaft 462 as shown in FIG. 16 such that the electrically conducting fluid tends to flow radially inward towards the target site, or it may be formed towards the center of shaft 462 (not shown) so that the fluid flows radially outward. In both of these embodiments, a fluid source (e.g., a bag of fluid elevated above the surgical site or having a pumping device), is coupled to catheter 460 via a fluid supply tube (not shown) that may or may not have a controllable valve.

In an alternative embodiment shown in FIG. 17A, the electrically conducting fluid is delivered from a fluid delivery element (not shown) that is separate from catheter 460. In arthroscopic surgery, for example, the body cavity will be flooded with isotonic saline and the catheter 460 will be introduced into this flooded cavity. Electrically conducting fluid will be continually resupplied to maintain the conduction path between return electrode 624 and electrode terminals 463.

Figure 18:
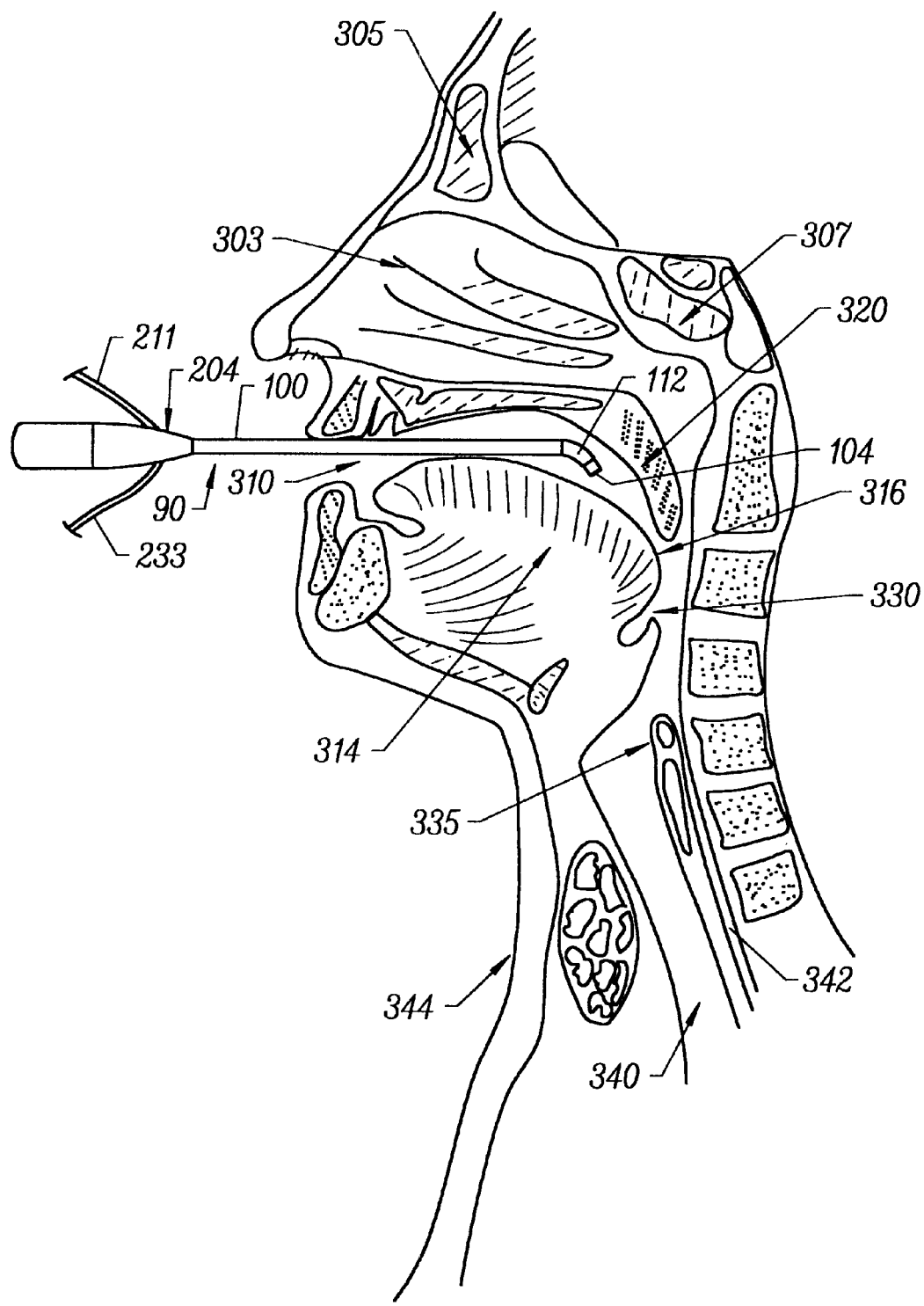
FIG. 18 illustrates a procedure for treating submucosal tissue according to the present invention.

Referring to FIGS. 18–21, methods for treating air passage disorders according to the present invention will now be described. In these embodiments, an electrosurgical probe such as one described above can be used to ablate targeted masses including, but not limited to, the tongue, tonsils, turbinates, soft palate tissues (e.g., the uvula), hard tissue and mucosal tissue. In one embodiment, selected portions of the tongue 314 are removed to treat sleep apnea or snoring. In this method, the distal end of an electrosurgical probe 90 is introduced into the patient's mouth 310, as shown in FIG. 18. If desired, an endoscope (not shown), or other type of viewing device, may also be introduced, or partially introduced, into the mouth 310 to allow the surgeon to view the procedure (the viewing device may be integral with, or separate from, the electrosurgical probe). The electrode terminals 104 are positioned adjacent to or against the back surface 316 of the target site, e.g., the tongue 314, and electrically conductive fluid is delivered to the target site, as described above. Alternatively, the conductive fluid is applied to the target site, or the distal end of probe 90 is dipped into conductive fluid or gel prior to introducing the probe 90 into the patient's mouth. The power supply 28 is then activated and adjusted such that a high frequency voltage difference is applied between electrode terminals 104 and return electrode 112 in the presence of the conductive fluid to remove selected portions of the back of the tongue 314, as described above, without damaging sensitive structures, such as nerves, and the bottom portion of the tongue 314.

In the preferred embodiment, the high frequency voltage is sufficient to convert the electrically conductive fluid (not shown) between the target tissue and electrode terminal(s) 104 into an ionized vapor layer or plasma. As a result of the applied voltage difference between electrode terminal(s) 140 and the target tissue, charged particles in the plasma are accelerated towards the occlusion to cause dissociation of the molecular bonds within tissue structures, as discussed above. During the process, products of ablation and excess electrically conductive fluid, and other fluids (e.g., blood) may be aspirated from the target site to facilitate the surgeon's view. During ablation of the tissue, the residual heat generated by the current flux lines (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure. Once the blockage has been removed, aeration and drainage are reestablished to allow the sinuses to heal and return to their normal function.

Depending on the procedure, the surgeon may translate the electrode terminals 104 relative to the target tissue to form holes, channels, stripes, divots, craters or the like within the tongue. In addition, the surgeon may purposely create some thermal damage within these holes, or channels to form scar tissue that will stiffen the target tissue, e.g., the tongue, and minimize air passage blockage after the procedure. In one embodiment, the physician axially translates the electrode terminals 104 into the tongue tissue as the tissue is volumetrically removed to form one or more holes in the turbinate, typically having a diameter of less than 2 mm, preferably less than 1 mm. In another embodiment, the physician translates the electrode terminals 104 across the outer surface 316 of the tongue 314 to form one or more channels or troughs. Applicant has found that the present invention can quickly and cleanly create such holes, divots or channels in tissue with the cold ablation technology described herein. A more complete description of methods for forming holes or channels in tissue can be found in U.S. Pat. No. 5,683,366, the complete disclosure of which is incorporated herein by reference for all purposes.

Another advantage of the present invention is the ability to precisely ablate channels or holes within the tissue without causing necrosis or thermal damage to the underlying and surrounding tissues, nerves (e.g., the optic nerve) or bone. In addition, the voltage can be controlled so that the energy directed to the target site is insufficient to ablate bone or adipose tissue (which generally has a higher impedance than the target sinus tissue). In this manner, the surgeon can literally clean the tissue off the bone, without ablating or otherwise effecting significant damage to the bone.

Figure 19:
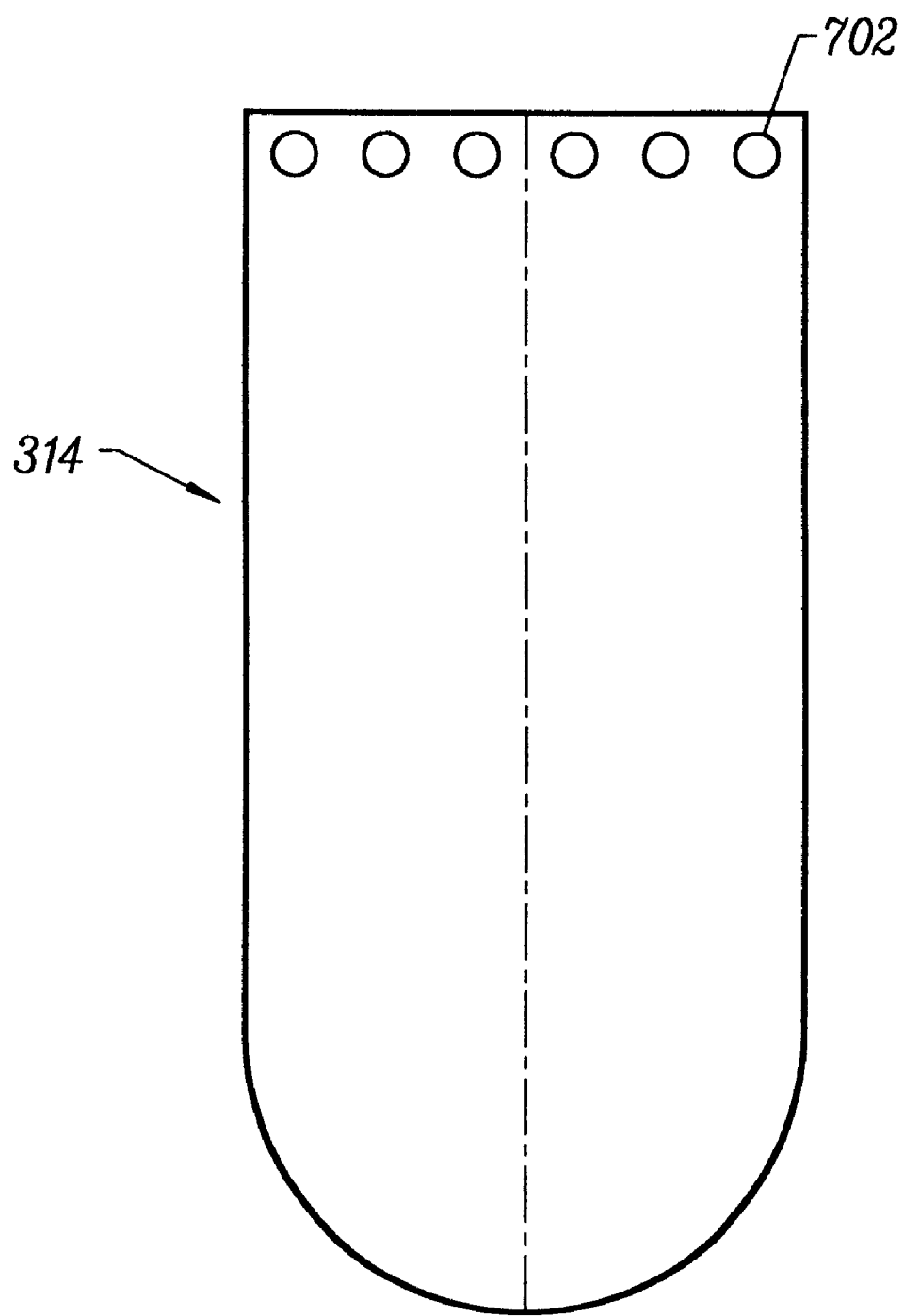
FIG. 19 is a top view of the tongue, illustrates a plurality of channels near the back of the tongue, generated with the techniques of the present invention.
Figure 20:
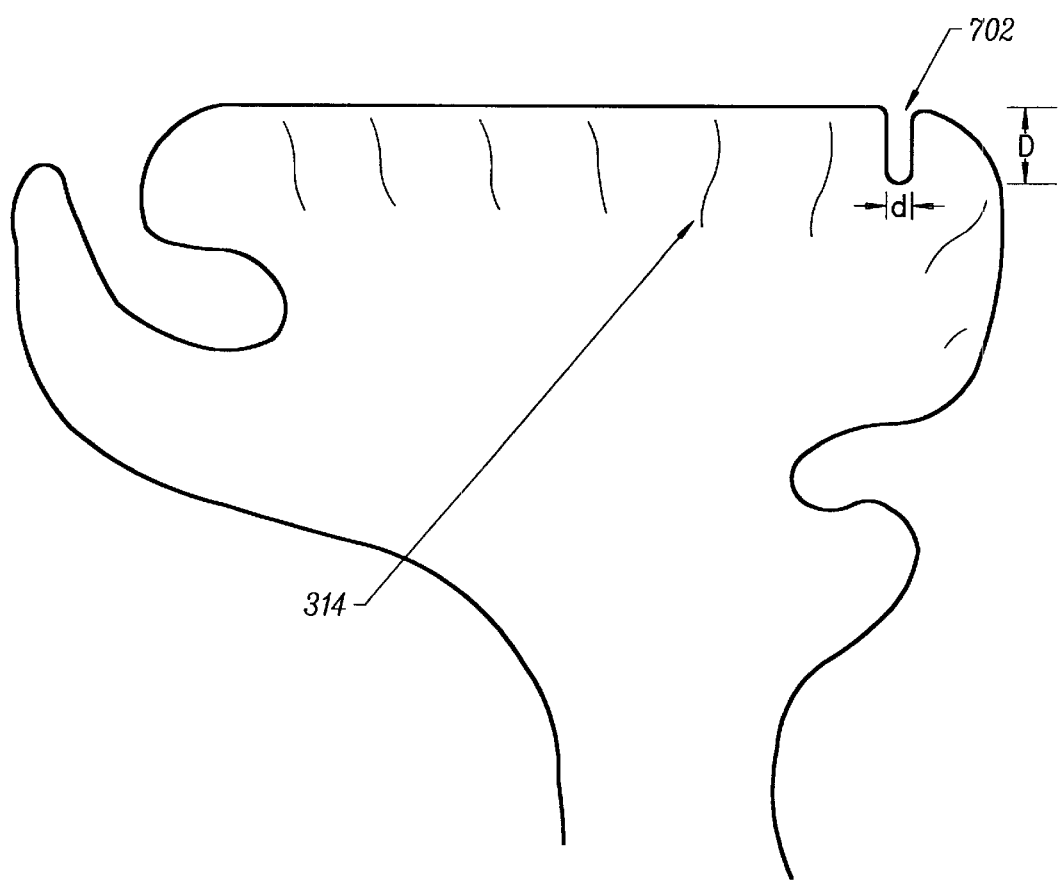
FIG. 20 is a side view of the tongue, illustrating a single channel.
Figure 21:
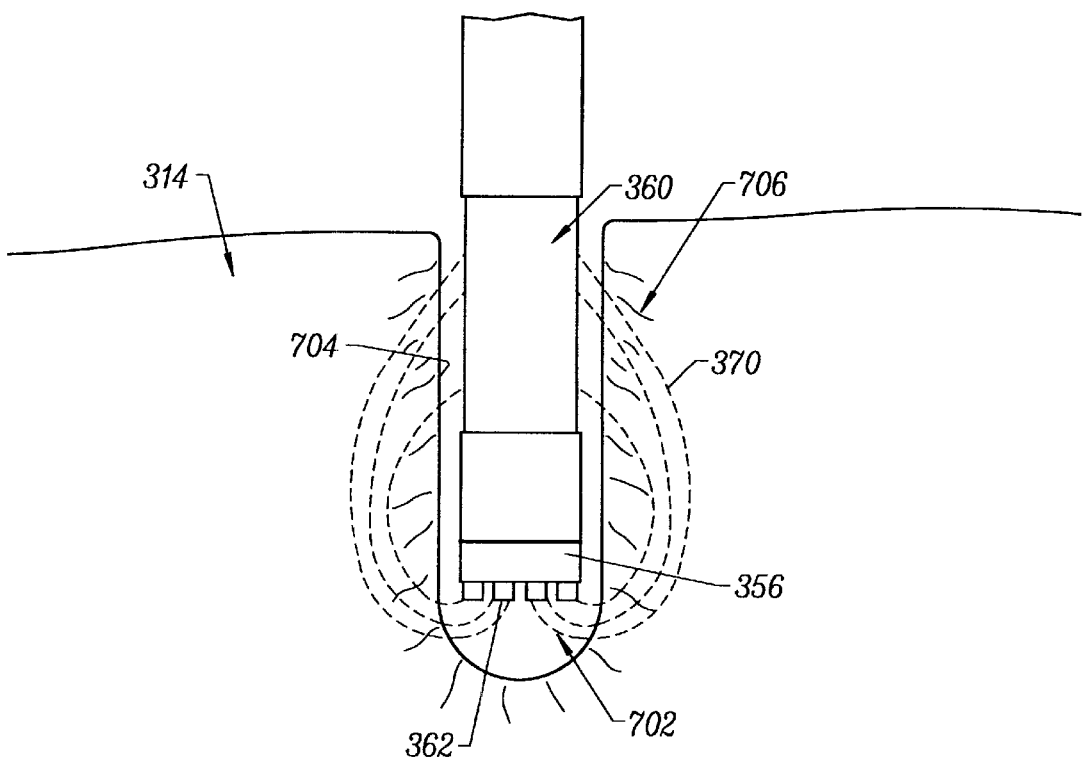
FIG. 21 is a detailed view of a single channel generated with the techniques of the present invention.

FIGS. 19–21 illustrate a specific method for treating obstructive sleep disorders by treating the back of the patient's tongue 314. In this procedure, a plurality of holes or channels 702 are formed in the back of the patient's tongue 314. Holes 702 are preferably formed with the methods described in detail above. Namely, a high frequency voltage difference is applied between active and return electrodes 362, 360, respectively, in the presence of an electrically conductive fluid. The fluid may be delivered to the target site, applied directly to the target site, or the distal end of the probe may be dipped into the fluid prior to the procedure. The voltage is sufficient to vaporize the fluid around active electrodes 362 to form a plasma with sufficient energy to effect molecular dissociation of the tissue. The distal end of the probe 350 is then axially advanced through the tissue as the tissue is removed by the plasma in front of the probe 350. As shown in FIGS. 19 and 20, holes 702 will typically have a depth D in the range of about 0.5 to 2.5 cm, preferably about 1.2 to 1.8 cm, and a diameter d of about 0.5 to 5 mm, preferably about 1.0 to 3.0 mm. The exact diameter will, of course, depend on the diameter of the electrosurgical probe used for the procedure.

Referring to FIG. 21, during the formation of each hole 702, the conductive fluid between active and return electrodes 362, 360 will generally minimize current flow into the surrounding tissue, thereby minimizing thermal damage to the tissue. Therefore, severed blood vessels in the surface 704 of the hole 702 may not be coagulated as the electrodes 362 advance through the tissue. In addition, in some procedures, it may be desired to thermally damage the surface 704 of the hole 702 to stiffen the tissue. Applicant has discovered that stiffening the tissue at the back of the tongue 314 reduces air passage obstruction after the procedure. For these reasons, it may be desired in some procedures to increase the thermal damage caused to the surface 704 of tongue. In one embodiment, the physician switches the electrosurgical system from the ablation mode to the subablation or thermal heating mode after the hole 702 has been formed. This is typically accomplished by pressing a switch or foot pedal to reduce the voltage applied to a level below the threshold required for ablation for the particular electrode configuration and the conductive fluid being used in the procedure (as described above). In the subablation mode, the physician will then remove the distal end of the probe 350 from the hole 702. As the probe is withdrawn, high frequency current flows from the active electrodes 362 through the surrounding tissue to the return electrode 360. This current flow heats the tissue and coagulates severed blood vessels at surface 704.

In some embodiments, it may be desired to increase the thermal damage of surface 704 to create scar tissue around the hole. In these embodiments, it may be necessary to either: (1) withdraw the probe 350 slowly, e.g., about 0.5 to 1.0 cm/sec; or (2) hold the probe 350 within the hole 702 for a period of time, e.g., on the order of 1 to 30 seconds, while in the subablation mode. The current flows through the tissue surrounding hole 702 during this time period and creates thermal damage therein. In the representative embodiment, the thermal necrosis 706 will extend about 1.0 to 5.0 mm from surface 704 of hole 702. In this embodiment, the probe may include one or more temperature sensors (not shown) on probe coupled to one or more temperature displays on the power supply 28 such that the physician is aware of the temperature within the hole 702 during the procedure.

In addition to the above procedures, the system and method of the present invention may be used for treating a variety of disorders in the mouth 310, pharynx 330, larynx 335, hypopharynx, trachea 340, esophagus 342 and the neck 344 (see FIG. 18). For example, tonsillar hyperplasis or other tonsil disorders may be treated with a tonsillectomy by partially ablating the lymphoepithelial tissue. This procedure is usually carried out under intubation anesthesia with the head extended. An incision is made in the anterior faucial pillar, and the connective tissue layer between the tonsillar parenchyma and the pharyngeal constrictor muscles is demonstrated. The incision may be made with conventional scalpels, or with the electrosurgical probe of the present invention. The tonsil is then freed by ablating through the upper pole to the base of the tongue, preserving the faucial pillars. The probe ablates the tissue, while providing simultaneous hemostasis of severed blood vessels in the region. Similarly, adenoid hyperplasia, or nasal obstruction leading to mouth breathing difficulty, can,be treated in an adenoidectomy by separating (e.g., resecting or ablating) the adenoid from the base of the nasopharynx.

Other pharyngeal disorders can be treated according to the present invention. For example, hypopharyngeal diverticulum involves small pouches that form within the esophagus immediately above the esophageal opening. The sac of the pouch may be removed endoscopically according to the present invention by introducing a rigid esophagoscope, and isolating the sac of the pouch. The cricopharyngeus muscle is then divided, and the pouch is ablated according to the present invention. Tumors within the mouth and pharynx, such as hemangionmas, lymphangiomas, papillomas, lingual thyroid tumors, or malignant tumors, may also be removed according to the present invention.

Other procedures of the present invention include removal of vocal cord polyps and lesions and partial or total laryngectomies. In the latter procedure, the entire larynx is removed from the base of the tongue to the trachea, if necessary with removal of parts of the tongue, the pharynx, the trachea and the thyroid gland.

Tracheal stenosis may also be treated according to the present invention. Acute and chronic stenoses within the wall of the trachea may cause coughing, cyanosis and choking.

Figure 24:
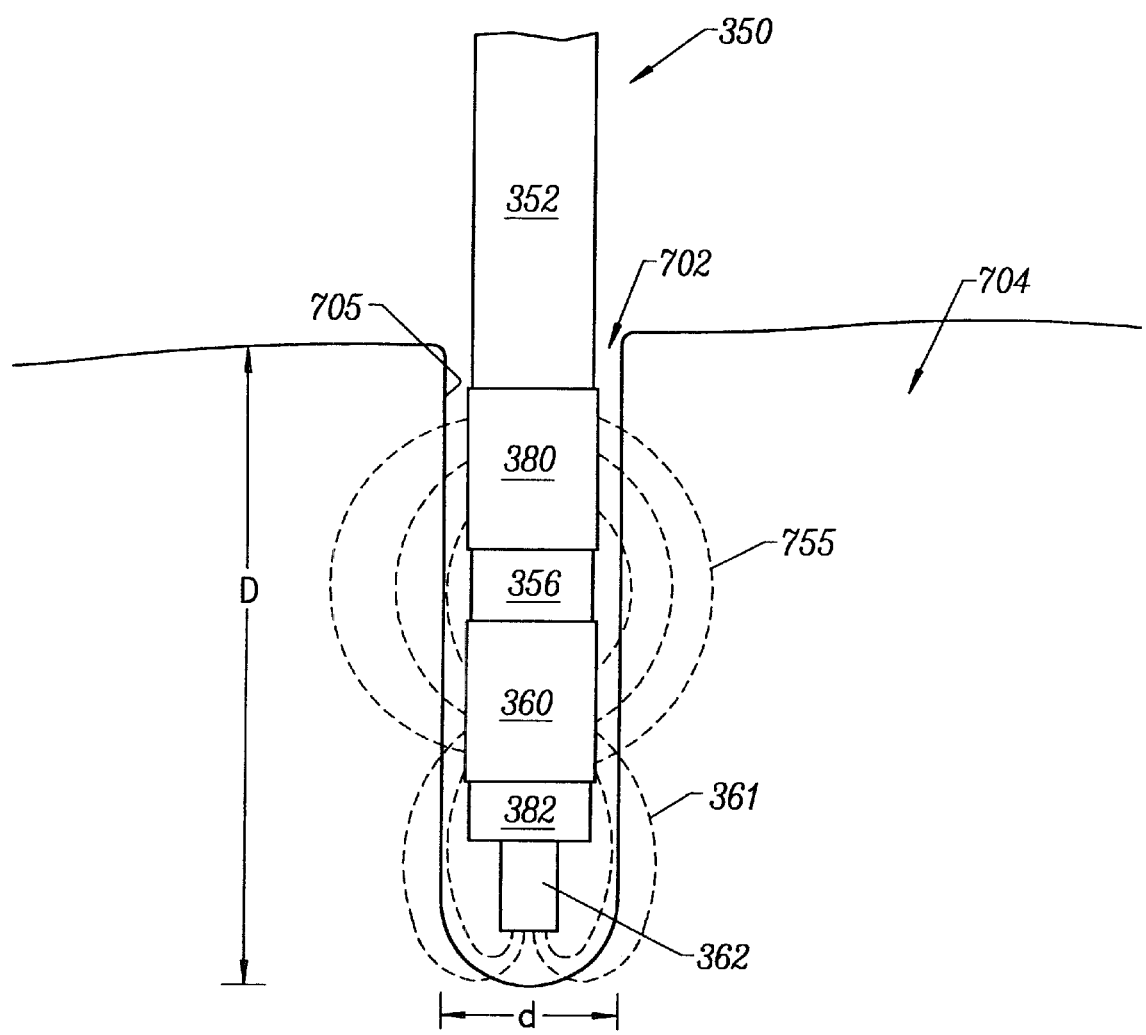
FIG. 24 illustrates a method for submucosal channeling with the probe of FIG. 12D.

FIG. 24 illustrates a specific method for treating tissue with the embodiment shown in FIG. 12D. Holes or channels 702 are preferably formed in the tissue, e.g., turbinates, soft palate tissue, tongue or tonsils, with the methods described in detail above. Namely, a high frequency voltage difference is applied between active and return electrodes 362, 360, respectively, in the presence of an electrically conductive fluid such that an electric current 361 passes from the active electrode 362, through the conductive fluid, to the return electrode 360. As shown in FIG. 24, this will result in shallow or no current penetration into the target tissue 704. The fluid may be delivered to the target site, applied directly to the target site, or the distal end of the probe may be dipped into the fluid prior to the procedure. The voltage is sufficient to vaporize the fluid around active electrode 362 to form a plasma with sufficient energy to effect molecular dissociation of the tissue. The distal end of the probe 350 is then axially advanced through the tissue as the tissue is removed by the plasma in front of the probe 350. The holes 702 will typically have a depth D in the range of about 0.5 to 2.5 cm, preferably about 1.2 to 1.8 cm, and a diameter d of about 0.5 to 5 mm, preferably about 1.0 to 3.0 mm. The exact diameter will, of course, depend on the diameter of the electrosurgical probe used for the procedure.

During the formation of each hole 702, the conductive fluid between active and return electrodes 362, 360 will generally minimize current flow into the surrounding tissue, thereby minimizing thermal damage to the tissue. Therefore, severed blood vessels on the surface 705 of the hole 702 may not be coagulated as the electrodes 362 advance through the tissue. In addition, in some procedures, it may be desired to thermally damage the surface 705 of the hole 702 to stiffen the tissue. For these reasons, it may be desired in some procedures to increase the thermal damage caused to the tissue surrounding hole 702. In the embodiment shown in FIG. 12D, it may be necessary to either: (1) withdraw the probe 350 slowly from hole 702 after coagulation electrode 380 has at least partially advanced past the outer surface of the disc tissue 704 into the hole 702 (as shown in FIG. 24); or (2) hold the probe 350 within the hole 702 for a period of time, e.g., on the order of 1 to 30 seconds. Once the coagulation electrode 380 is in contact with, or adjacent to, tissue, electric current 755 flows through the tissue surrounding hole 702 and creates thermal damage therein. The coagulation and return electrodes 380, 360 both have relatively large, smooth exposed surfaces to minimize high current densities at their surfaces, which minimizes damage to the surface 705 of hole. Meanwhile, the size and spacing of these electrodes 360, 380 allows for relatively deep current penetration into the tissue 704. In the representative embodiment, the thermal necrosis will extend about 1.0 to 5.0 mm from surface 705 of hole 702. In this embodiment, the probe may include one or more temperature sensors (not shown) on probe coupled to one or more temperature displays on the power supply 28 such that the physician is aware of the temperature within the hole 702 during the procedure.

What is claimed is:

1. A method for treating tissue comprising:
   positioning an active electrode adjacent to tissue;
   applying a first high frequency voltage between the active electrode and a return electrode;
   during at least a portion of the applying step, advancing the active electrode into the tissue; and
   during or after the first applying step, applying a second high frequency voltage between the return electrode and a coagulation electrode.

2. The method of claim 1 wherein the first and second high frequency voltages are the same.

3. The method of claim 1 wherein the second high frequency voltage is lower than the first high frequency voltage.

4. The method of claim 1 wherein the active electrode, return electrode and coagulation electrode are spaced from each other on an instrument shaft, the advancing step comprising advancing the active and return electrodes into the tissue.

5. The method of claim 4 wherein the advancing step further comprising advancing the coagulation electrode to at least the surface of the tissue such that at least a portion of the coagulation electrode is in contact with the tissue.

6. The method of claim 5 wherein the first and second high frequency voltages are the same voltage, the method further comprising applying the same voltage between the active electrode and the return and coagulation electrodes while maintaining the active, return and coagulation electrodes in contact with the tissue.

7. The method of claim 6 wherein the maintaining step is carried out for about 1 to 20 seconds, the method further comprising withdrawing the active, return and coagulation electrodes from the tissue after the maintaining step.

8. The method of claim 5 wherein the first and second high frequency voltages are the same voltage, the method further comprising applying the same voltage between the active electrode and the return and coagulation electrodes while withdrawing the active, return and coagulation electrodes from the tissue.

9. The method of claim 1 wherein the tissue is selected from the group consisting of the tonsils, palate, uvula, turbinates, pharynx and the tongue.

10. The method of claim 1 further comprising providing an electrically conductive fluid around the active electrode and between the active and return electrodes prior to the first applying step.

11. The method of claim 10 wherein the providing step comprises positioning the active and return electrodes within a source of the electrically conductive fluid and then positioning the active and return electrodes adjacent to the tissue.

12. The method of claim 10 wherein the providing step comprises delivering the electrically conductive fluid to the active and return electrodes.

13. The method of claim 10 further comprising generating a current flow path between the active and return electrodes with the electrically conductive fluid.

14. The method of claim 1 wherein the first high frequency voltage is sufficient to ablate the tissue structure and the second high frequency voltage is sufficient to thermally damage a surface of the tissue structure in contact with the return and coagulation electrodes.

15. The method of claim 1 further comprising axially translating the active electrode to form a hole through at least a portion of the tissue structure.

16. The method of claim 15 wherein the hole has a maximum lateral dimension less than about 2 mm.

17. A system for treating tissue comprising:

an electrosurgical instrument having a shaft with a proximal end portion and a distal end portion;

an electrode assembly comprising first, second and third electrodes positioned on the distal end portion of the shaft and axially spaced from each other;

a power source coupled to the first, second and third electrodes for applying a high frequency voltage between the first and second electrodes, and between the second and third electrodes at the same time.

18. The system of claim 17 wherein the distal end portion of the shaft is sized for delivery through a percutaneous opening in the patient to a spinal disc.

19. The system of claim 17 wherein the third electrode comprises an annular band spaced proximally from the second electrode and having a substantially smooth, exposed surface to reduce current densities on said surface.

20. The system of claim 19 wherein the exposed surface of the third electrode has a larger surface area than an exposed surface of the first and second electrodes.

21. The system of claim 17 wherein the third electrode has an exposed length in the range of about 2.0 to 8.0 mm, and the second electrode has an exposed length in the range of about 2.0 to 8.0 mm.

22. The system of claim 17 further including a first insulating member positioned between the first and second electrodes and a second insulating member between the second and third electrodes.

23. The system of claim 17 further comprising a fluid delivery element for delivering electrically conductive fluid to the first and second electrodes.

24. The system of claim 17 wherein the fluid delivery element comprises a lumen extending adjacent to, or through, the shaft, and a distal opening on the shaft coupled to the lumen.

25. The system of claim 17 further comprising a fluid aspiration element for aspirating fluid from a region around the first electrode.

* * * * *